US 8,063,104 B2

(12) United States Patent
Vallance et al.

(10) Patent No.: US 8,063,104 B2
(45) Date of Patent: Nov. 22, 2011

(54) GUANIDINE DERIVATIVES AS INHIBITORS OF DDAH

(75) Inventors: Patrick John Thompson Vallance, London (GB); James Mitchell Leiper, London (GB); David Lawrence Selwood, London (GB); Sharon Rossiter, Hatfield Herts (GB); Basil Hartzoulakis, Cambridge (GB)

(73) Assignee: UCL Business PLC, London (GB)

( * ) Notice: Subject to any disclaimer, the term of this patent is extended or adjusted under 35 U.S.C. 154(b) by 296 days.

(21) Appl. No.: 11/719,208

(22) PCT Filed: Nov. 11, 2005

(86) PCT No.: PCT/GB2005/004361
§ 371 (c)(1),
(2), (4) Date: Oct. 24, 2007

(87) PCT Pub. No.: WO2006/051314
PCT Pub. Date: May 18, 2006

(65) Prior Publication Data
US 2009/0069331 A1    Mar. 12, 2009

(30) Foreign Application Priority Data

Nov. 12, 2004  (GB) .................................... 0425039.5
May 20, 2005  (GB) .................................... 0510348.6

(51) Int. Cl.
C07C 279/14 (2006.01)
C07C 279/12 (2006.01)
A61K 31/223 (2006.01)
A61K 31/195 (2006.01)

(52) U.S. Cl. ......... 514/565; 514/551; 560/169; 562/560
(58) Field of Classification Search .................. 564/230, 564/240; 514/551, 565; 560/169; 562/560
See application file for complete search history.

(56) References Cited

U.S. PATENT DOCUMENTS

| | | | |
|---|---|---|---|
| 4,530,920 A | 7/1985 | Nestor et al. | |
| 4,659,693 A | 4/1987 | Nestor | |
| 4,686,283 A | 8/1987 | Nestor, Jr. et al. | |
| 4,789,681 A | 12/1988 | Sportoletti et al. | |
| 5,318,992 A | 6/1994 | Whitten et al. | |
| 5,352,796 A | 10/1994 | Hoeger et al. | |
| 5,554,638 A | 9/1996 | Dewhirst et al. | |
| 5,859,295 A | 1/1999 | Crooks et al. | |
| 5,972,940 A | 10/1999 | Broquet et al. | |
| 6,716,436 B1 * | 4/2004 | Seguin ........................... 424/401 |
| 2002/0156129 A1 | 10/2002 | Kuraishi et al. | |

FOREIGN PATENT DOCUMENTS

| | | |
|---|---|---|
| EP | 0097031 | 12/1983 |
| EP | 0472220 | 2/1992 |
| EP | 1022268 | 7/2000 |
| EP | 1038864 | 9/2000 |
| WO | WO-99/31052 | 6/1999 |
| WO | WO-0004058 | 1/2000 |
| WO | WO-00/40548 | 7/2000 |
| WO | WO-00/51623 | 9/2000 |
| WO | WO-03097085 | 11/2003 |
| WO | WO-2006/051314 | 5/2006 |

OTHER PUBLICATIONS

Atkinson et al. Bioorg. Med. Chem. Lett. 1999, 9, 2953-2958.*
Rossiter et al. J. Med. Chem. 2005, 48, 4670-4678.*
Jordan, V. C. Nature Reviews: Drug Discovery, 2, 2003, pp. 205-213.*
Luo et al. (Cell, 2009, 136, pp. 823-837).*
Atkinson et al., "Guanidine-Substituted Imidazoles as Inhibitors of Nitric Oxide Synthase"; Bioorganic and Medicinal Chemistry Letters; Oct. 18, 1999; 2953-2958; vol. 9(20).
Database CA [Online] Chemical Abstract Service, Columbus, Ohio, US, Phuket et al., Synthesis and structure-activity studies of some antitumor congeners of L-canavanine XP002374544; Database accession No. 1997:628412; abstract; Drug Development Research; vol. 40(4); 1997 325-332.
Database CA [Online] Chemical Abstract Service, Columbus, Ohio, Kennedy et al; "A facile route to cyclic and acyclic alkylarginines"; XP002374545; Database accession No. 1998:138426; abstract; Synthetic Communications; vol. 28 (4); 1998; 741-746.
Database Caplus [Online] Chemical Abstract Services, Columbus, Ohio, US; Hevelke et al., "Synthesis of arginine peptides with N7, N8-(1, 2-dihydroxycyclohex-1, 2-ylene) protection. Reaction of 1, 2-cyclohexanedione with arginine and lysine"; XP002374543; Database accession No. 1982:616659; Monatshefte Fuer Chemie; vol. 113 (4); 1982; 457-473.
Kennedy et al., "Design rationale, synthesis, and characterization of non-natural analogs of the cationic amino acids arginine and lysine"; J Pept Res.; Apr. 2000; 348-58; vol. 55(4).
Nestor et al., "Potent, long-acting luteinizing hormone-releasing hormone antagonists containing new synthetic amino acids: N,N'-dialkyl-D-homoarginines", J Med Chem. Jan. 1988; 65-72; vol. 31(1).
Olken et al., "NG-allyl- and NG-cyclopropyl-L-arginine: two novel inhibitors of macrophage nitric oxide synthase"; J-Med-Chem; Mar. 20, 1992; 1137-44; vol. 35(6).
Patthy et al., "Reversible modification of arginine residues. Application to sequence studies by restriction of tryptic hydrolysis to lysine residues"; J Biol Chem.; Jan. 25, 1975; 557-564; vol. 250(2).

(Continued)

*Primary Examiner* — Joseph Kosack
*Assistant Examiner* — Matthew Coughlin
(74) *Attorney, Agent, or Firm* — Fulbright & Jaworski, L.L.P.

(57) ABSTRACT

Compounds of formula (I) have been found to be useful as inhibitors of DDAH. The present invention thus provides the use of a compound of formula (I), or a pharmaceutically acceptable salt thereof, in the manufacture of a medicament for use in the treatment of a disease whose pathology is affected by DDAH 14 Claims, 3 Drawing Sheets

OTHER PUBLICATIONS

Robertson et al., "Inhibition of Bovine Brain Nitric Oxide synthase"; Bioorganic Chemistry; 1995; 144-151; vol. 23.

Rossiter et al., "Selective substrate-based inhibitors of mammalian dimethylarginine dimethylaminohydrolase"; J Med Chem.; Jul. 14, 2005; 4670-8; vol. 48(14).

Shlomo et al., "Synthesis of Guandino-N-Alkylarginines by the use of Polymeric Psedoureas"; J. Org. Cem.; 1981; 808-809; XP002374531; vol. 46.

Wagenaar et al., "Methodology for the Preparation of N-Guanidino-Modified Arginines and Related Derivatives", J. Org. Chem.; 1993; 4331-4338; vol. 58 (1).

Zhang et al., "Potent and selective inhibition of neuronal nitric oxide synthase by N omega-propyl-L-arginine", J-Med-Chem.; Nov. 21, 1997; 3869-70; 40(24): vol. 40(24).

Bredt et al., "Nitric oxide mediates glutamate-linked enhancement of cGMP levels in the cerebellum", Proc Natl Acad Sci U S A., Nov. 1989; 9030-9033, vol. 86(22).

Dawson et al, "A microtiter-plate assay of human NOS Isoforms", Methods in Molecular Biology, 1998, 237-242, vol. 100.

Feichtinger et al., "Triurethane-Protected Guanidines and Triflyldiurethane-Protected Guanidines: New Reagents for Guanidinylation Reactions", J. Org. Chem., 1998, 8432-8439, vol. 63 (23).

Hullan et al., "The hydrazine derivative aminoguanidine inhibits the reaction of tetrahydrofolic acid with hydroxymethylarginine biomolecule", Acta-Biol-Hung., 1998; 265-73, vol. 49(2-4).

Kostourou et al., "Dimethylarginine dimethylaminohydrolase I enhances tumour growth and angiogenesis", British Journal of Cancer, 2002, 673-680, vol. 87.

Kostourou et al., "Effects of overexpression of dimethylarginine dimethylaminohydrolase on tumour angiogenesis assessed by susceptibility Magnetic resonance imaging", Cancer Res., 2003, 4960-4699, vol. 63.

Leiper et al., "Biological significance of endogenous methylarginines that inhibit nitric oxide synthases", Cardiovasc Res., Aug. 15, 1999; 542-8, vol. 43(3).

Macallister et al., "Regulation of nitric oxide synthesis by dimethylarginine dimethylaminohydrolase", Br J Pharmacol., Dec. 1996; 1533-1540, vol. 119(8).

Ogawa et al., "Purification and properties of a new enzyme, NG,NG-dimethylarginine dimethylaminohydrolase, from rat kidney", J. Biol. Chem., Jun. 1989, 10205-10209, vol. 264(17).

Okuno et al., "Accumulated endogenous nitric oxide synthase inhibitors in inhibiting urethral relaxation following estrogen supplementation in ovariectomized rabbits", The Journal of Urology, Jul. 2004, 360-364, vol. 172(1).

Robinson et al., "Animal models for target and/or drug evaluation", "Overexpression of dimethylarginine dimethylaminohydrolase (ddah) enhances tumor growth, angiogenesis and hypoxia", Clinical Cancer Research, Dec. 2003, vol. 9(Poster Session C, No. C26).

Smith et al., "Dimethylarginine dimethylaminohydrolase activity modulates ADMA levels, VEGF expression, and cell phenotype", Biochemical and Biophysical Research Communications, 2003, 984-989, vol. 308 (4).

Thuring et al., "Comparative study of the active site caging of serine proteases: thrombin and factor Xa", Biochemistry, Feb. 12, 2002; 2002-13, vol. 41(6).

Leiper, James et al.; "Disruption of methylarginine metabolism impairs vascular homeostasis"; NATURE MEDICINE; Feb. 2007; vol. 13, No. 2; pp. 198-203.

Applicant's Table Showing Additional Results.

* cited by examiner

GUANIDINE DERIVATIVES AS INHIBITORS OF DDAH

CROSS-REFERENCE TO RELATED APPLICATIONS

This application is the National Stage Application of International Application Number PCT/GB05/004361 filed on Nov. 11, 2005, assigned the International Publication Number WO 2006/051314 A2 published on May 18, 2006, which claims priority to Great Britain Patent Application No. 0510348.6 filed May 20, 2005 and to Great Britain Patent Application No. 0425039.5 filed on Nov. 12, 2004.

TECHNICAL FIELD

The present invention relates to compounds that are inhibitors of DDAH and which are therefore useful in treating diseases whose pathology is affected by DDAH.

BACKGROUND OF THE INVENTION

Endogenous methylarginines $N^G N^G$ dimethyl-L-arginine (ADMA) and $N^G$ monomethyl-L-arginine (L-NMMA) which are released by proteolysis of methylated protein arginine residues, are inhibitors of all nitric oxide synthase (NOS) isoforms. The enzyme dimethylarginine dimethylaminohydrolase (DDAH) metabolises the two NOS-inhibiting methylarginines, but not the related $N^G N'^G$ dimethylarginine (SDMA) which is physiologically inactive.

Thus DDAH, which controls levels of asymmetrically methylated arginine derivatives, may have therapeutic potential through its ability to indirectly influence the activity of NOS.

BRIEF SUMMARY OF THE INVENTION

It has now surprisingly been found that compounds of the general formula (I) set out below act as inhibitors of DDAH. Accordingly, the present invention provides the use of a compound of formula (I), or a pharmaceutically acceptable salt thereof, in the manufacture of a medicament for use as an inhibitor of DDAH

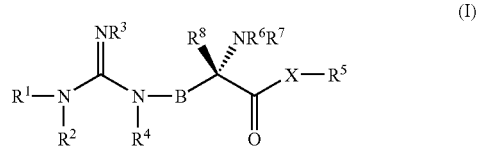

(I)

wherein:
either (a) $R^1$ is $C_3$-$C_{12}$ alkyl, $C_3$-$C_{12}$ alkenyl, $C_3$-$C_{12}$ alkynyl, $C_6$-$C_{10}$ aryl, $C_3$-$C_8$ carbocyclyl, 5- to 10-membered heterocyclyl, 5- to 10-membered heteroaryl, -L-A, -L-Het-L', -L-Y-L', -L-Het-A or -L-Y-A, wherein:
L is $C_1$-$C_6$ alkyl, $C_2$-$C_6$ alkenyl or $C_2$-$C_6$ alkynyl;
L' is $C_1$-$C_6$ alkyl, $C_2$-$C_6$ alkenyl or $C_2$-$C_6$ alkynyl;
A is $C_6$-$C_{10}$ aryl, $C_3$-$C_8$ carbocyclyl, 5- to 10-membered heterocyclyl or 5- to 10-membered heteroaryl;
Het is —O—, —S— or —NR'—, wherein R' is hydrogen, $C_1$-$C_6$ alkyl, $C_2$-$C_6$ alkenyl, $C_2$-$C_6$ alkynyl; and
Y is —CO—, —SO—, —SO$_2$—, —CO—O—, —CO—NR'—, —O—CO— or —NR'—CO—, wherein R' is as defined above;

$R^2$ is hydrogen, $C_1$-$C_6$ alkyl, $C_2$-$C_6$ alkenyl or $C_2$-$C_6$ alkynyl; and
$R^3$ is hydrogen, $C_1$-$C_6$ alkyl, $C_2$-$C_6$ alkenyl or $C_2$-$C_6$ alkynyl,
or (b) $R^1$ and $R^2$ form, together with the nitrogen to which they are attached, a 5- to 10-membered heterocyclic or heteroaryl ring, and $R^3$ is as defined above,
or (c) $R^1$ and $R^3$ form, together with the —N—C=N— moiety to which they are attached, a 5 to 10-membered heterocyclic or heteroaryl ring, and $R^2$ is as defined above;
$R^4$ is hydrogen, $C_1$-$C_6$ alkyl, $C_2$-$C_6$ alkenyl or $C_2$-$C_6$ alkynyl;
B is $C_1$-$C_6$ alkyl, $C_2$-$C_6$ alkenyl, —O-L-, —S-L- or -L-Het-L'-, wherein L, L' and Het are as defined above;
X is —O—, —S— or —NR'—, wherein R' is as defined above;
$R^5$ is hydrogen, $C_1$-$C_6$ alkyl, $C_2$-$C_6$ alkenyl, $C_2$-$C_6$ alkynyl, aryl, $C_3$-$C_8$ carbocyclyl, 5- to 10-membered heterocyclyl, 5- to 10-membered heteroaryl, -L-A, -L-Het-L', -L-Y-L', -L-Het-A, -L-Y-A, -L-A-Het-A, -L-A-L'-A or -L-A-Het-L'-A, wherein L, L', Het and Y are as defined above and wherein each A is the same or different and is as defined above;
$R^6$ is hydrogen, $C_1$-$C_6$ alkyl, $C_2$-$C_6$ alkenyl or $C_2$-$C_6$ alkynyl;
$R^7$ is hydrogen, $C_1$-$C_6$ alkyl, $C_2$-$C_6$ alkenyl or $C_2$-$C_6$ alkynyl, or $R^7$ is a bond, a $C_1$-$C_4$ alkyl or $C_2$-$C_4$ alkenyl moiety which is joined to one of the carbon atoms of B to form, together with the —N—C— moiety to which $R^7$ and B are attached, a 5- to 10-membered heterocyclic ring; and
$R^8$ is hydrogen, $C_1$-$C_6$ alkyl, $C_2$-$C_6$ alkenyl or $C_2$-$C_6$ alkynyl;
wherein:
the alkyl, alkenyl and alkynyl groups and moieties in the substituents $R^1$ to $R^7$, X and B are unsubstituted or substituted by one, two or three substituents which are the same or different and are selected from halogen, hydroxy, amino and thio substituents; and
the aryl, carbocyclyl, heterocyclyl and heteroaryl groups and moieties in the substituents $R^1$ and $R^5$, the heterocyclic or heteroaryl moieties formed by $R^1$ together with $R^2$ and $R^1$ together with $R^3$ and heterocyclic moieties formed by $R^7$ together with B are unsubstituted or substituted by one, two or three substituents selected from halogen, hydroxy, amino, thio, $C_1$-$C_6$ alkyl, $C_1$-$C_6$ alkoxy, $C_1$-$C_6$ alkylthio, nitro, cyano, $C_1$-$C_6$ alkylamino, di-($C_1$-$C_6$ alkyl)amino, $C_1$-$C_6$ haloalkyl, $C_1$-$C_6$ haloalkoxy and $C_1$-$C_6$ haloalkylthio substituents.

Examples of compounds of formula (I) are compounds as defined above wherein $R^5$ is hydrogen, $C_1$-$C_6$ alkyl, $C_2$-$C_6$ alkenyl, $C_2$-$C_6$ alkynyl, aryl, $C_3$-$C_8$ carbocyclyl, 5- to 10-membered heterocyclyl, 5- to 10-membered heteroaryl, -L-A, -L-Het-L', -L-Y-L', -L-Het-A or -L-Y-A, wherein L, L', A, Het and Y are as defined above.

The present invention also relates to a compound of formula (I) for use in the manufacture of a medicament for use in the treatment of a disease whose pathology is affected by DDAH.

The present invention also relates to a compound of formula (I) for use in the manufacture of a medicament for use in the treatment of ischaemia-reperfusion injury of the brain or heart, cancer, lethal hypotension in severe inflammatory conditions, local and systemic inflammatory disorders, neurodegeneration, asthma, pain or sepsis.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
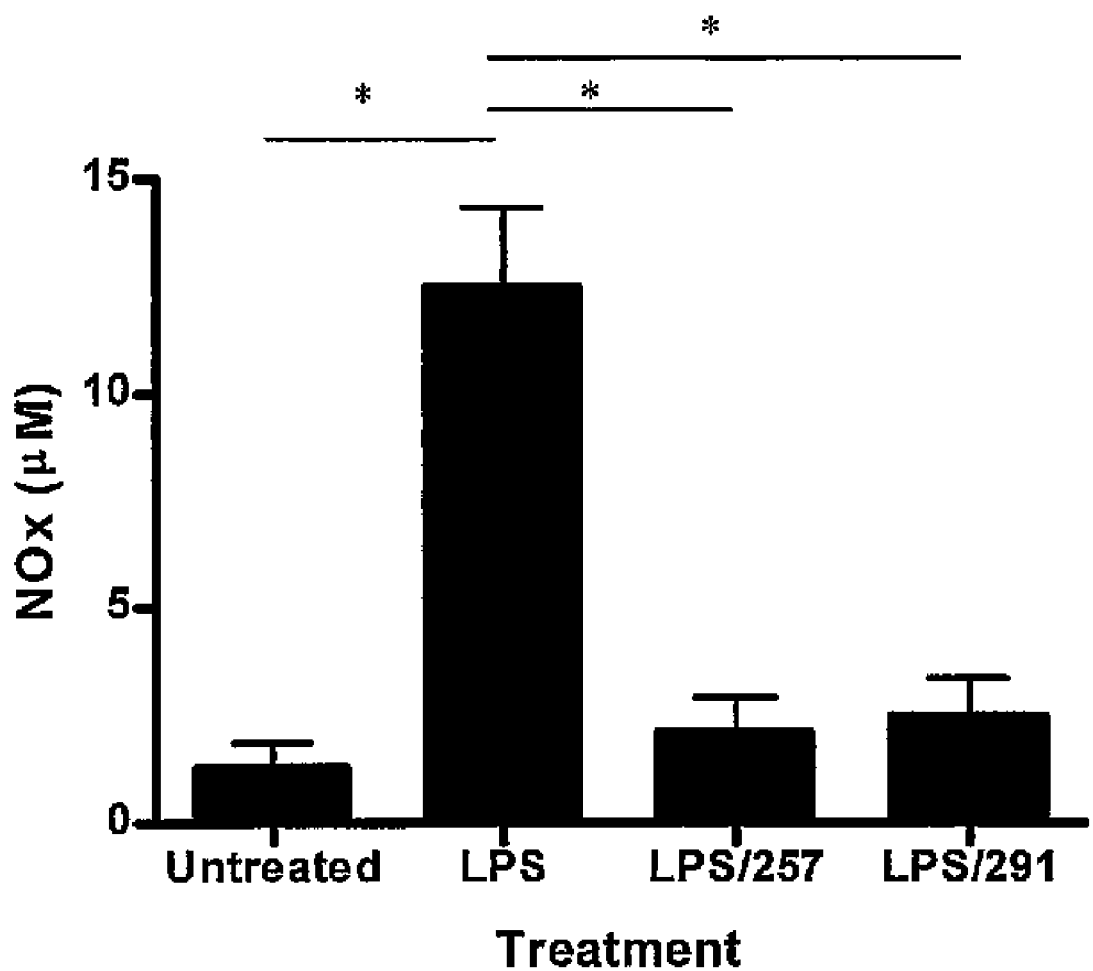
FIG. 1 is a graph showing the nitrate and nitrite (NOx) production from isolated rat aortic rings in static culture in the presence of either media alone (untreated); media plus 10 μg/ml LPS (LPS) and media plus 10 μg/ml LPS and 500 μM SR257 or SR291. n≧6; *p<0.0001 One Way ANOVA plus Bonferroni post hoc correction.

The present invention relates to the use of a compound of formula (I), or a pharmaceutically acceptable salt thereof, in the manufacture of a medicament for use as an inhibitor of DDAH.

For the avoidance of doubt, the orientation of the group Y in the moiety -L-Y-A is such that the left hand side of the depicted group is attached to L. Thus, for example, when Y is —CO—NR'—, the group -L-Y-A is -L-CO—NR'-A. Similarly, for the avoidance of doubt, the orientation of the group Y in the moiety -L-Y-L' is such that the left hand side of the depicted group is to L. Thus, for example, when Y is —CO—NR'—, the group -L-Y-L' is -L-CO—NR'-L'.

For the avoidance of doubt, when the group B is —O-L- or —S-L- the left hand side of the depicted group is attached to the guanadine nitrogen. Thus, for example, when B is —O-L-, the moiety —R$^4$N—B—CR$^8$(NR$^6$R$^7$)— is —R$^4$N—O-L-CR$^8$(NR$^6$R$^7$)—.

As used herein, a $C_1$-$C_{12}$ alkyl group or moiety is a linear or branched alkyl group or moiety containing from 1 to 12 carbon atoms, such as a $C_3$-$C_{12}$, a $C_1$-$C_6$ or $C_1$-$C_4$ alkyl group or moiety. Examples of such alkyl groups or moieties are methyl, ethyl, n-propyl, i-propyl, n-butyl, n-octyl and —CH$_2$CMe$_3$. Examples of $C_3$-$C_{12}$ alkyl groups or moieties are n-propyl, i-propyl, n-butyl, n-octyl and —CH$_2$CMe$_3$. In one embodiment, a $C_3$-$C_{12}$ alkyl group is preferably a $C_5$-$C_{12}$ alkyl group and more preferably a $C_6$-$C_{12}$ alkyl group. A divalent alkyl group or moiety (or alkylene group or moiety) can be attached via the same carbon atom, via adjacent carbon atoms or via non-adjacent carbon atoms. Examples of divalent alkyl moieties are methylene, 1,2-ethyl and 1,3-propyl moieties. Preferred divalent alkyl moieties are 1,2-ethyl and 1,3-propyl moieties.

As used herein, a $C_2$-$C_{12}$ alkenyl group or moiety is a linear or branched alkenyl group or moiety containing from 2 to 12 carbon atoms, such as a $C_3$-$C_{12}$, $C_2$-$C_6$ or $C_2$-$C_4$ alkenyl group or moiety, for example ethenyl, n-propenyl and n-butynyl. A preferred $C_2$-$C_6$ alkenyl group is ethenyl. A preferred $C_3$-$C_{12}$ alkenyl group is allyl. In one embodiment, a $C_3$-$C_{12}$ alkenyl group is preferably a $C_4$-$C_{12}$ alkenyl group and more preferably a $C_5$-$C_{12}$ alkenyl group. Typically an alkenyl group has only one double bond. This double bond is typically located at the α-position of the alkenyl group. A divalent alkenyl group (or alkenylene group) can be attached via the same carbon atom, via adjacent carbon atoms or via non-adjacent carbon atoms.

As used herein, a $C_2$-$C_{12}$ alkynyl group or moiety is a linear or branched alkenyl group or moiety containing from 2 to 12 carbon atoms, such as a $C_3$-$C_{12}$, $C_2$-$C_6$ or $C_2$-$C_4$ alkynyl group or moiety, for example ethynyl. In one embodiment, a $C_3$-$C_{12}$ alkynyl group is preferably a $C_4$-$C_{12}$ alkynyl group and more preferably a $C_5$-$C_{12}$ alkynyl group. Typically an alkynyl group has only one triple bond. This triple bond is typically located at the α-position of the alkynyl group. A divalent alkynyl group (or alkynylene group) can be attached via the same carbon atom, via adjacent carbon atoms or via non-adjacent carbon atoms.

As used herein, a halogen is typically chlorine, fluorine, bromine or iodine and is preferably chlorine or fluorine. As used herein, a said $C_1$-$C_6$ alkoxy group is typically a said $C_1$-$C_6$ alkyl group attached to an oxygen atom. A said $C_1$-$C_6$ alkylthio group is typically a said $C_1$-$C_6$ alkyl group attached to a thio group.

As used herein, a $C_1$-$C_6$ haloalkyl group is typically a said $C_1$-$C_6$ alkyl group, for example a $C_1$-$C_4$ alkyl group, substituted by one or more said halogen atoms. Typically, it is substituted by 1, 2 or 3 said halogen atoms. Examples of haloalkyl groups include perhaloalkyl groups such as —CX$_3$ wherein X is a said halogen atom, for example —CF$_3$. Preferred haloalkyl groups include monohaloalkyl groups such as —CH$_2$—CH$_2$F and perhaloalkyl groups such as —CF$_3$. Examples of preferred haloalkyl groups include monohaloalkyl groups such as —CH$_2$—CH$_2$F.

As used herein, a $C_1$-$C_6$ haloalkoxy group is typically a said $C_1$-$C_6$ alkoxy group, for example a $C_1$-$C_4$ alkoxy group, substituted by one or more said halogen atoms. Typically, it is substituted by 1, 2 or 3 said halogen atoms. Preferred haloalkoxy groups include perhaloalkoxy groups such as —OCX$_3$ wherein X is a said halogen atom. Particularly preferred haloalkoxy groups are —OCF$_3$ and —OCCl$_3$.

As used herein, a $C_1$-$C_6$ haloalkylthio group is typically a said $C_1$-$C_6$ alkylthio group, for example a $C_1$-$C_4$ alkylthio group, substituted by one or more said halogen atoms. Typically, it is substituted by 1, 2 or 3 said halogen atoms. Preferred haloalkylthio groups include perhaloalkylthio groups such as —$SCX_3$ wherein X is a said halogen atom. Particularly preferred haloalkylthio groups are —$SCF_3$ and —$SCCl_3$.

As used herein, a $C_3$-$C_6$ carbocyclyl group or moiety is a non-aromatic saturated or unsaturated hydrocarbon ring, having from 3 to 6 carbon atoms. Preferably it is a saturated group, i.e. a $C_3$-$C_6$ cycloalkyl group. Examples include cyclopropyl, cyclobutyl, cyclopentyl and cyclohexyl. Preferred carbocyclyl groups are cyclopropyl and cyclohexyl. In one embodiment, a $C_3$-$C_6$ carbocyclyl group is preferably a $C_4$-$C_6$ carbocyclyl group and more preferably a $C_5$-$C_6$ carbocyclyl group.

As used herein, a 5- to 10-membered heterocyclyl group or moiety is a non-aromatic, saturated or unsaturated $C_5$-$C_{10}$ carbocyclic ring, for example a 5- or 6-membered ring, in which one or more, for example 1, 2 or 3, of the carbon atoms are replaced by a heteroatom selected from N, O and S. Saturated heterocyclyl groups are preferred. Examples of suitable heterocyclyl groups include piperidinyl, piperazinyl, morpholinyl, pyrrolidinyl, tetrahydrofuranyl, imidazolidinyl, thiazolidinyl, 1,4 dioxanyl, 1,3 dioxolanyl and dihydroimidazolyl. Preferred heterocyclyl groups are piperidinyl, morpholinyl, pyrrolidinyl, tetrahydrofuranyl and dihydroimidazolyl. Examples of preferred heterocyclyl groups are piperidinyl, morpholinyl, pyrrolidinyl and dihydroimidazolyl. Particularly preferred heterocyclyl groups are piperidinyl, morpholinyl, tetrahydrofuranyl and pyrrolidinyl. Examples of particularly preferred heterocyclyl groups are piperidinyl, morpholinyl and pyrrolidinyl.

As used herein, a $C_6$-$C_{10}$ aryl group or moiety is typically a phenyl or naphthyl group or moiety. Preferably, it is a phenyl moiety.

As used herein, a 5- to 10-membered heteroaryl group is a 5- to 10-membered aromatic ring, such as a 5- or 6-membered ring, containing at least one heteroatom, for example 1, 2 or 3 heteroatoms, selected from O, S and N. Examples include pyridyl, pyrazinyl, pyrimidinyl, pyridazinyl, furanyl, thienyl, imidazolyl, pyrazolidinyl, pyrrolyl, oxadiazolyl, oxazolyl, isoxazolyl, thiadiazolyl, thiazolyl and pyrazolyl groups. Thienyl groups are preferred.

Typically, the alkyl, alkenyl and alkynyl groups and moieties in the substituents $R^1$ to $R^7$, X and B are unsubstituted or substituted by one, two or three substituents which are the same or different and are selected from fluorine, chlorine, bromine, hydroxy, amino and thio substituents. Preferably, the alkyl, alkenyl and alkynyl groups and moieties in the substituents $R^1$ to $R^7$, X and B are unsubstituted or substituted by a single hydroxy substituent or by one, two or three substituents which are the same or different and are selected from fluorine and chlorine substituents. More preferably, the alkyl, alkenyl and alkynyl groups and moieties in the substituents $R^1$ to $R^7$, X and B are unsubstituted or substituted by a single fluoro substituent.

Typically, when a said aryl, heteroaryl, heterocyclyl or carbocyclyl group or moiety carries a nitro or cyano substituent, only one of the substituents on the aryl, heteroaryl, heterocyclyl, or carbocyclyl group is a nitro or cyano group. Further, the aryl, carbocyclyl, heterocyclyl and heteroaryl groups and moieties in the substituents $R^1$ and $R^5$, the heterocyclic or heteroaryl moieties formed by $R^1$ together with $R^2$ and $R^1$ together with $R^3$ and the heterocyclic moieties formed by $R^7$ together with B are typically unsubstituted or substituted by one, two or three substituents selected from fluorine, chlorine, bromine, hydroxy, amino, thio, $C_1$-$C_4$ alkyl, $C_1$-$C_4$ alkoxy, $C_1$-$C_4$ alkylthio, $C_1$-$C_4$ alkylamino, di-($C_1$-$C_4$ alkyl) amino, $C_1$-$C_4$ haloalkyl, $C_1$-$C_4$ haloalkoxy and $C_1$-$C_4$ haloalkylthio substituents.

Preferably, the aryl, carbocyclyl, heterocyclyl and heteroaryl groups and moieties in the substituents $R^1$ and $R^5$, the heterocyclic or heteroaryl moieties formed by $R^1$ together with $R^2$ and $R^1$ together with $R^3$ and the heterocyclic moieties formed by $R^7$ together with B are typically unsubstituted or substituted by one, two or three substituents selected from fluorine, chlorine, hydroxy, $C_1$-$C_4$ alkyl, $C_1$-$C_4$ alkoxy and $C_1$-$C_4$ haloalkyl substituents.

More preferably, the aryl, carbocyclyl, heterocyclyl and heteroaryl groups and moieties in the substituents $R^1$, the heterocyclic or heteroaryl moieties formed by $R^1$ together with $R^2$ and $R^1$ together with $R^3$ and the heterocyclic moieties formed by $R^7$ together with B are unsubstituted and the aryl, carbocyclyl, heterocyclyl and heteroaryl groups and moieties in the substituent $R^5$ are unsubstituted or substituted by one or two substituents selected from fluorine, $C_1$-$C_2$ alkyl, $C_1$-$C_2$ alkoxy and $C_1$-$C_2$ haloalkyl substituents.

It is further preferred that the aryl, carbocyclyl, heterocyclyl and heteroaryl groups and moieties in the substituents $R^1$ and $R^5$, the heterocyclic or heteroaryl moieties formed by $R^1$ together with $R^2$ and $R^1$ together with $R^3$ and the heterocyclic moieties formed by $R^7$ together with B are unsubstituted.

Typically, the substituents on the aryl, carbocyclyl, heterocyclyl and heteroaryl groups and moieties are themselves unsubstituted.

Typically, R' in the or each Het or Y moiety is hydrogen or $C_1$-$C_6$ alkyl. Preferably, R' in the or each Het or Y moiety is hydrogen or $C_1$-$C_4$ alkyl. More preferably, R' in the or each Het or Y moiety is hydrogen or methyl.

Typically, L in the or each $R^1$, $R^5$ or B moiety is $C_1$-$C_6$ alkyl. Preferably, L in the or each $R^1$, $R^5$ or B moiety is $C_1$-$C_4$ alkyl. More preferably, L in the or each $R^1$, $R^5$ or B moiety is $C_1$-$C_2$ alkyl.

Typically, L' in the or each $R^1$, $R^5$ or B moiety is $C_1$-$C_6$ alkyl. Preferably, L' in the or each $R^1$, $R^5$ or B moiety is $C_1$-$C_4$ alkyl. More preferably, L' in the or each $R^1$, $R^5$ or B moiety is $C_1$-$C_2$ alkyl.

Typically, A in the or each $R^1$ or $R^5$ moiety is phenyl, $C_3$-$C_6$ carbocyclyl, 5- to 6-membered heterocyclyl or 5- to 6-membered heteroaryl. Preferably, A in the or each $R^1$ or $R^5$ moiety is phenyl, 5- to 6-membered heterocyclyl or 5- to 6-membered heteroaryl. Examples of preferred A groups in the or each $R^1$ or $R^5$ moiety are phenyl and 5- to 6-membered heteroaryl. More preferably, A in the or each $R^1$ or $R^5$ moiety is phenyl, tetrahydrofuranyl or thienyl. Examples of more preferred A groups in the or each $R^1$ or $R^5$ moiety are phenyl and thienyl.

Typically, Het in the or each $R^1$, $R^5$ or B moiety is —O—, —S— or —NR'—, wherein R' is as defined above. Preferably, Het in the or each $R^1$, $R^5$ or B moiety is —O—, —S— or —NMe-.

Typically, Y in the or each $R^1$ or $R^5$ moiety is —CO—, —SO—, —$SO_2$—, —CO—O—, —CO—NR'—, —O—CO— or —NR'—CO—, wherein R' is as defined above. Preferably, Y in the or each $R^1$ or $R^5$ moiety is —CO—, —CO—O— or —CO—NR'—, wherein R' is as defined above. More preferably, Y in the or each $R^1$ or $R^5$ moiety is —CO—, —CO—O—, —CO—NH— or —CO—NMe-.

Typically, -L-Y-L' in the or each $R^1$ or $R^5$ moiety is —($C_1$-$C_6$ alkyl)-Y—($C_1$-$C_6$ alkyl), wherein Y is as defined above. Preferably, -L-Y-L' in the or each $R^1$ or $R^5$ moiety is —($C_1$-$C_4$ alkyl)-Y—($C_1$-$C_4$ alkyl), wherein Y is as defined above. More preferably, -L-Y-L' in the or each $R^1$ or $R^5$ moiety is —($C_1$-$C_2$ alkyl)-CO—($C_1$-$C_2$ alkyl), —($C_1$-$C_2$ alkyl)-CO—O—($C_1$-$C_2$ alkyl), —($C_1$-$C_2$ alkyl)-CO—NH—($C_1$-$C_2$ alkyl) or —($C_1$-$C_2$ alkyl)-CO-NMe-($C_1$-$C_2$ alkyl).

Typically, -L-Het-L' in the or each $R^1$ or $R^5$ moiety is —($C_1$-$C_6$ alkyl)-Het-($C_1$-$C_6$ alkyl), wherein Het is as defined above. Preferably, -L-Het-L' in the or each $R^1$ or $R^5$ moiety is —($C_1$-$C_4$ alkyl)-Het-($C_1$-$C_4$ alkyl), wherein Het is as defined above. More preferably, -L-Het-L' in the or each $R^1$ or $R^5$ moiety is —($C_1$-$C_2$ alkyl)-O—($C_1$-$C_4$ alkyl), —($C_1$-$C_2$ alkyl)-S—($C_1$-$C_2$ alkyl) or —($C_1$-$C_2$ alkyl)-NMe-($C_1$-$C_2$ alkyl).

Typically, -L-Het-A in the or each $R^1$ or $R^5$ moiety is —($C_1$-$C_6$ alkyl)-Het-A, wherein Het and A are as defined above. Preferably, -L-Het-A in the or each $R^1$ or $R^5$ moiety is —($C_1$-$C_4$ alkyl)-Het-A, wherein Het is as defined above and A is a phenyl or 5- to 6-membered heteroaryl group. More preferably, -L-Het-A in the or each $R^1$ or $R^5$ moiety is —($C_1$-$C_2$ alkyl)-O-phenyl.

Typically, -L-Y-A in the or each $R^1$ or $R^5$ moiety is —($C_1$-$C_6$ alkyl)-Y-A, wherein Y and A are as defined above. Preferably, -L-Y-A in the or each $R^1$ or $R^5$ moiety is —($C_1$-$C_4$ alkyl)-Y-A, wherein Y is as defined above and A is a phenyl or 5- to 6-membered heteroaryl group. More preferably, -L-Het-A in the or each $R^1$ or $R^5$ moiety is —($C_1$-$C_2$ alkyl)-CO-phenyl, —($C_1$-$C_2$ alkyl)-CO—O-phenyl, —($C_1$-$C_2$ alkyl)-CO—NH-phenyl or —($C_1$-$C_2$ alkyl)-CO-NMe-phenyl.

Typically, -L-A in the or each $R^1$ or $R^5$ moiety is —($C_1$-$C_6$ alkyl)-A, wherein A is as defined above. Preferably, -L-A in the or each $R^1$ or $R^5$ moiety is —($C_1$-$C_4$ alkyl)-A, wherein A is a phenyl, 5- to 6-membered heterocyclyl or 5- to 6-membered heteroaryl group. An example of a preferred -L-A in the or each $R^1$ or $R^5$ moiety is —($C_1$-$C_4$ alkyl)-A, wherein A is a phenyl or 5- to 6-membered heteroaryl group. More preferably, -L-A in the $R^1$ moiety is —($C_1$-$C_2$ alkyl)-phenyl, —($C_1$-$C_2$ alkyl)-tetrahydrofuranyl or —($C_1$-$C_2$ alkyl)-thienyl. Examples of more preferred -L-A in the $R^1$ moiety is —($C_1$-$C_2$ alkyl)-phenyl or —($C_1$-$C_2$ alkyl)-thienyl. Further, more preferably, -L-A in the $R^5$ moiety is —($C_1$-$C_2$ alkyl)-phenyl.

Typically, -L-A-Het-A in the $R^5$ moiety is —($C_1$-$C_6$ alkyl)-A-Het-A wherein Het is as defined above and each A is the same or different and is as defined above. Preferably, -L-A-Het-A in the $R^5$ moiety is —($C_1$-$C_4$ alkyl)-A-Het-A, wherein Het is as defined above and each A is the same or different and is a phenyl or 5- to 6-membered heteroaryl group. More preferably, -L-A-Het-A in the $R^5$ moiety is —($C_1$-$C_2$ alkyl)-phenyl-O-phenyl.

Typically, $R^1$ is $C_3$-$C_8$ alkyl, $C_3$-$C_8$ alkenyl, $C_3$-$C_8$ alkynyl, phenyl, $C_3$-$C_6$ carbocyclyl, 5- to 6-membered heterocyclyl, 5- to 6-membered heteroaryl, -L-A, -L-Het-L', -L-Y-L', -L-Het-A or -L-Y-A, wherein L, L', A, Het and Y are as defined above.

Preferably, R' is $C_3$-$C_8$ alkyl, $C_3$-$C_6$ alkenyl, phenyl, $C_3$-$C_6$ carbocyclyl, 5- to 6-membered heterocyclyl, 5- to 6-membered heteroaryl, -L-A, -L-Het-L' or -L-Het-A, wherein L, L', A and Het are as defined above.

In one embodiment, R' is preferably phenyl, 5- to 6-membered heterocyclyl, 5- to 6-membered heteroaryl, -L-A, -L-Het-L' or -L-Het-A, wherein L, L', A and Het are as defined above. It is particularly preferred that R' is -L-Het-L' or -L-Het-A, wherein L, L', A and Het are as defined above. It is more preferred that R' is -L-Het-L' wherein L, L' and Het are as defined above. It is further preferred that R' is —($C_1$-$C_4$ alkyl)-Het-($C_1$-$C_4$ alkyl), wherein Het is —O—, —S— or —NMe-.

More preferably, $R^1$ is $C_3$-$C_8$ alkyl, allyl, phenyl, cyclopropyl, cyclohexyl, —($C_1$-$C_2$ alkyl)-phenyl, —($C_1$-$C_2$ alkyl)-thienyl, —($C_1$-$C_2$ alkyl)-tetrahydrofuranyl, —($C_1$-$C_2$ alkyl)-O-phenyl, —($C_1$-$C_2$ alkyl)-O—($C_1$-$C_4$ alkyl), —($C_1$-$C_2$ alkyl)-S—($C_1$-$C_2$ alkyl) or —($C_1$-$C_2$ alkyl)-NMe-($C_1$-$C_2$ alkyl). Examples of more preferred $R^1$ groups are $C_3$-$C_8$ alkyl, allyl, phenyl, cyclopropyl, cyclohexyl, —($C_1$-$C_2$ alkyl)-phenyl, —($C_1$-$C_2$ alkyl)-thienyl, —($C_1$-$C_2$ alkyl)-O-phenyl, —($C_1$-$C_2$ alkyl)-O—($C_1$-$C_4$ alkyl), —($C_1$-$C_2$ alkyl)-S—($C_1$-$C_2$ alkyl) and —($C_1$-$C_2$ alkyl)-NMe-($C_1$-$C_2$ alkyl).

Typically, $R^2$ is hydrogen or $C_1$-$C_6$ alkyl. Preferably, $R^2$ is hydrogen or $C_1$-$C_4$ alkyl. More preferably, $R^2$ is hydrogen, methyl or ethyl.

Typically, $R^3$ is hydrogen or $C_1$-$C_6$ alkyl. Preferably, $R^3$ is hydrogen or $C_1$-$C_2$ alkyl. More preferably, $R^3$ is hydrogen.

When $R^1$ and $R^2$ form, together with the nitrogen to which they are attached, a 5- to 10-membered heterocyclic or heteroaryl ring, they typically form a 5- to 6-membered heterocyclic or heteroaryl ring. Preferably, they form a 5- to 6-membered heterocyclic ring. Examples of such rings are piperidinyl, morpholinyl and pyrrolidinyl rings. Typically, said heterocyclic and heteroaryl rings are unsubstituted.

When $R^1$ and $R^3$ form, together with the —N—C=N— moiety to which they are attached, a 5- to 10-membered heterocyclic or heteroaryl ring, they typically form a 5- to 6-membered heterocyclic or heteroaryl ring. Preferably, they form a 5- to 6-membered heterocyclic ring. Examples of such rings are dihydroimidazole and tetrahydropyrimidine rings with dihydroimidazole rings being preferred. Typically, said heterocyclic and heteroaryl rings are unsubstituted.

Typically, $R^4$ is hydrogen or $C_1$-$C_6$ alkyl. Preferably, $R^4$ is hydrogen or $C_1$-$C_2$ alkyl. More preferably, $R^4$ is hydrogen.

Typically, -L-Het-L'- in the moiety B is —($C_1$-$C_4$ alkyl)-Het-($C_1$-$C_4$ alkyl)-, wherein Het is as defined above. Preferably, -L-Het-L'- in the moiety B is —($C_1$-$C_2$ alkyl)-Het-($C_1$-$C_2$ alkyl)-, wherein Het is as defined above.

Typically, —O-L- in the moiety B is —O—($C_1$-$C_4$ alkyl)-. Preferably, —O-L- in the moiety B is —O—($C_1$-$C_2$ alkyl)-.

Typically, —S-L- in the moiety B is —S—($C_1$-$C_4$ alkyl)-. Preferably, —S-L- in the moiety B is —S—($C_1$-$C_2$ alkyl)-.

Typically, B is $C_2$-$C_6$ alkyl. Preferably, B is $C_2$-$C_4$ alkyl. More preferably, B is 1,2-ethyl or 1,3-propyl. In a preferred embodiment, B is unsubstituted.

Typically, X is —O—, —S— or —NR'—, wherein R' is as defined above. Preferably, X is —O— or —NH—. Most preferably, X is —O—.

Typically, $R^5$ is hydrogen, $C_1$-$C_6$ alkyl, $C_2$-$C_6$ alkenyl, phenyl, $C_3$-$C_6$ carbocyclyl, 5- to 6-membered heterocyclyl, 5- to 6-membered heteroaryl, -L-A, -L-Het-L', -L-Y-L', -L-Het-A, -L-Y-A or -L-A-Het-A, wherein L, L', Het and Y are as defined above and wherein each A is the same or different and is as defined above. Examples of typical $R^5$ groups are hydrogen, $C_1$-$C_6$ alkyl, $C_2$-$C_6$ alkenyl, phenyl, $C_3$-$C_6$ carbocyclyl, 5- to 6-membered heterocyclyl, 5- to 6-membered heteroaryl, -L-A, -L-Het-L', -L-Y-L', -L-Het-A and L-Y-A, wherein L, L', A, Het and Y are as defined above. Preferably, $R^5$ is hydrogen, $C_1$-$C_6$ alkyl, phenyl, $C_3$-$C_6$ carbocyclyl, 5- to 6-membered heterocyclyl, 5- to 6-membered heteroaryl, -L-A, -L-Het-L', -L-Het-A or -L-A-Het-A, wherein L, L', and Het are as defined above and wherein each A is the same or different and is as defined above. Examples of preferred $R^5$ groups are hydrogen, $C_1$-$C_6$ alkyl, phenyl, $C_3$-$C_6$ carbocyclyl, 5- to 6-membered heterocyclyl, 5- to 6-membered heteroaryl, -L-A, -L-Het-L' and -L-Het-A, wherein L, L', A and Het are as defined above. More preferably, $R^5$ is hydrogen, $C_1$-$C_4$ alkyl or —($C_1$-$C_2$ alkyl)-phenyl, —($C_1$-$C_2$ alkyl)-O—($C_1$-$C_2$ alkyl) or —($C_1$-$C_2$ alkyl)-phenyl-O-phenyl. Examples of more preferred $R^5$ groups are hydrogen, $C_1$-$C_4$ alkyl and —($C_1$-$C_2$)-phenyl.

Typically, $R^6$ is hydrogen or $C_1$-$C_6$ alkyl. Preferably, $R^6$ is hydrogen or $C_1$-$C_2$ alkyl. More preferably, $R^6$ is hydrogen.

Typically, $R^7$ is hydrogen or $C_1$-$C_6$ alkyl. Preferably, $R^7$ is hydrogen or $C_1$-$C_2$ alkyl. More preferably, $R^7$ is hydrogen.

When $R^7$ is a bond, a $C_1$-$C_4$ alkyl or $C_2$-$C_4$ alkenyl moiety which is joined to one of the carbon atoms of B to form, together with the —N—C— moiety to which $R^7$ and B are attached, a 5- to 10-membered heterocyclic ring, it typically forms a 5- to 6-membered heterocyclic ring such as a pyrrolidine or piperidine ring. Pyrrolidine rings are preferred. Typically, said heterocyclic rings are unsubstituted.

When $R^7$ is a bond, a $C_1$-$C_4$ alkyl or $C_2$-$C_4$ alkenyl moiety which is joined to one of the carbon atoms of B to form, together with the —N—C— moiety to which $R^7$ and B are attached, a 5- to 10-membered heterocyclic ring, $R^7$ is typically a bond, or a $C_1$-$C_4$ alkyl moiety. Preferably, $R^7$ is a $C_1$-$C_2$ alkyl moiety.

Typically, $R^8$ is hydrogen or $C_1$-$C_6$ alkyl. Preferably, $R^8$ is hydrogen or $C_1$-$C_2$ alkyl. More preferably, $R^8$ is hydrogen.

In one embodiment of the present invention, the moiety

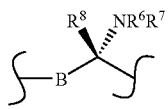

in the compounds of formula (J) typically represents

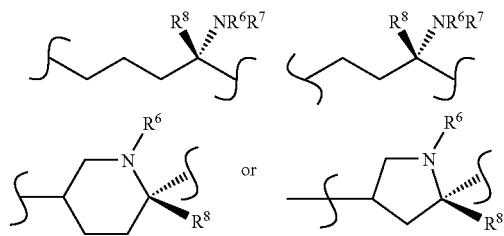

preferably represents

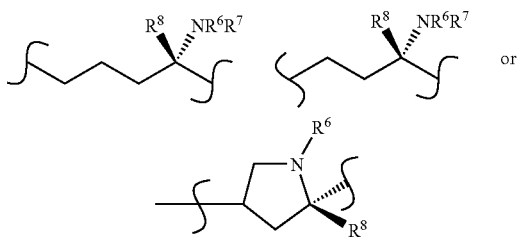

and more preferably represents

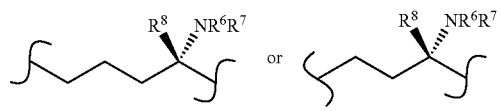

wherein $R^6$, $R^7$ and $R^8$ are as defined above.

In one embodiment, the compound of formula (I) is not $N^G$-allyl-L-arginine or $N^G$-cyclopropyl-L-arginine. In a second embodiment, the compound of formula (I) is not $N^G$-allyl-L-arginine, $N^G$-propyl-L-arginine or $N^G$-propargyl-L-arginine. In a further embodiment, the compound of formula (I) is not $N^G$-propyl-L-arginine or $N^G$-butyl-L-arginine. In a preferred embodiment, the compound of formula (I) is not AG-propyl-L-arginine, $N^G$-allyl-L-arginine, $N^G$-propargyl-L-arginine, $N^G$-butyl-L-arginine or $N^G$-cyclopropyl-L-arginine. More specifically, if the compound of formula (J) is used in the manufacture of a medicament for use in the treatment of pruritus, it is preferred that the compound of formula (I) is not $N^G$-allyl-L-arginine or $N^G$-cyclopropyl-L-arginine. If the compound of formula (I) is used in the manufacture of a medicament for use in the treatment of stroke, Alzheimer's disease and other neurodegenerative diseases, septic shock, inflammatory arthritis or colitis, it is preferred that the compound of formula (I) is not e-allyl-L-arginine, $N^G$-propyl-L-arginine or $N^G$-propargyl-L-arginine. If the compound of formula (I) is used in the manufacture of a medicament for use in the treatment of solid tumors, it is preferred that the compound of formula (I) is not $N^G$-propyl-L-arginine or $N^G$-butyl-L-arginine.

Preferred compounds of formula (I) are those wherein:
either (a) $R^1$ is $C_3$-$C_8$ alkyl, $C_3$-$C_8$ alkenyl, $C_3$-$C_8$ alkynyl, phenyl, $C_3$-$C_6$ carbocyclyl, 5- to 6-membered heterocyclyl, 5- to 6-membered heteroaryl,
-L-A, -L-Het-L', -L-Y-L', -L-Het-A or -L-Y-A, wherein:
L is $C_1$-$C_6$ alkyl;
L' is $C_1$-$C_6$ alkyl;
A is phenyl, $C_3$-$C_6$ carbocyclyl, 5- to 6-membered heterocyclyl or 5- to 6-membered heteroaryl;
Het is —O—, —S— or —NR'—, wherein R' is hydrogen or $C_1$-$C_6$ alkyl; and
Y is —CO—, —SO—, —SO$_2$—, —CO—O—, —CO—NR'—, —O—CO— or —NR'—CO—, wherein R' is as defined above;
$R^2$ is hydrogen or $C_1$-$C_6$ alkyl
$R^3$ is hydrogen or $C_1$-$C_6$ alkyl.
or (b) $R^1$ and $R^2$ form, together with the nitrogen to which they are attached, a 5- to 6-membered heterocyclic or heteroaryl ring, and $R^3$ is as defined above;
or (c) $R^1$ and $R^3$ form, together with the —N—C═N— moiety to which they are attached, a 5- to 6-membered heterocyclic or heteroaryl ring, and $R^2$ is as defined above;
$R^4$ is hydrogen or $C_1$-$C_6$ alkyl;
B is $C_2$-$C_6$ alkyl;
X is —O—, —S— or —NR'—, wherein R' is as defined above;
$R^5$ is hydrogen, $C_1$-$C_6$ alkyl, $C_2$-$C_6$ alkenyl, phenyl, $C_3$-$C_6$ carbocyclyl, 5- to 6-membered heterocyclyl, 5- to 6-membered heteroaryl, -L-A, -L-Het-L', -L-Y-L', -L-Het-A, -L-Y-A or -L-A-Het-A, wherein L, L', Het and Y are as defined above and wherein each A is the same or different and is as defined above;
$R^6$ is hydrogen or $C_1$-$C_6$ alkyl;
$R^7$ is hydrogen or $C_1$-$C_6$ alkyl or $R^7$ is a bond, a $C_1$-$C_4$ alkyl or $C_2$-$C_4$ alkenyl moiety which is joined to one of the carbon atoms of B to form, together with the —N—C— moiety to which $R^7$ and B are attached, a 5- to 6-membered heterocyclic ring; and
$R^8$ is hydrogen or $C_1$-$C_6$ alkyl,
wherein:
the alkyl, alkenyl and alkynyl groups and moieties in the substituents $R^1$ to $R^7$, X and B are unsubstituted or substituted by one, two or three substituents which are the same or different and are selected from fluorine, chlorine, bromine, hydroxy, amino and thio substituents; and the aryl, carbocyclyl, heterocyclyl and heteroaryl groups and moieties in the substituents $R^1$ and $R^5$, the heterocyclic or heteroaryl moieties formed by $R^1$ together with $R^2$ and $R^1$ together with $R^3$ and the heterocyclic moieties formed by $R^7$ together with B are typically unsubstituted or substituted by one, two or three substituents selected from fluorine, chlorine, bromine, hydroxy, amino, thio, $C_1$-$C_4$ alkyl, $C_1$-$C_4$ alkoxy, $C_1$-$C_4$ alkylthio, $C_1$-$C_4$ alkylamino, di-($C_1$-$C_4$ alkyl)amino, $C_1$-$C_4$ haloalkyl, $C_1$-$C_4$ haloalkoxy and $C_1$-$C_4$ haloalkylthio substituents.

Examples of such compounds are the preferred compounds of formula (I) as defined above wherein $R^5$ is hydrogen, $C_1$-$C_6$ alkyl, $C_2$-$C_6$ alkenyl, phenyl, $C_3$-$C_6$ carbocyclyl, 5- to 6-membered heterocyclyl, 5- to 6-membered heteroaryl, -L-A, -L-Het-L', -L-Y-L', -L-Het-A or L-Y-A, wherein L, L', A, Het and Y are as defined above.

More preferred compounds of formula (I) are those wherein:
either (a) $R^1$ is $C_3$-$C_8$ alkyl, $C_3$-$C_6$ alkenyl, phenyl, $C_3$-$C_6$ carbocyclyl, 5- to 6-membered heterocyclyl, 5- to 6-membered heteroaryl, -L-A, -L-Het-L' or -L-Het-A, wherein:
L is $C_1$-$C_4$ alkyl;
L' is $C_1$-$C_4$ alkyl;
A is phenyl, 5- to 6-membered heterocyclyl or 5- to 6-membered heteroaryl;
Het is —O—, —S— or —NMe-;
$R^2$ is hydrogen or $C_1$-$C_4$ alkyl;
$R^3$ is hydrogen or $C_1$-$C_2$ alkyl;
or (b) $R^1$ and $R^2$ form, together with the nitrogen to which they are attached, a 5- to 6-membered heterocyclic ring and $R^3$ is as defined above;
or (c) $R^1$ and $R^3$ form, together with the —N—C=N— moiety to which they are attached, a 5- to 6-membered heterocyclic ring and $R^2$ is as defined above;
$R^4$ is hydrogen or $C_1$-$C_2$ alkyl;
B is $C_2$-$C_4$ alkyl;
X is —O— or —NH—;
$R^5$ is hydrogen, $C_1$-$C_6$ alkyl, phenyl, $C_3$-$C_6$ carbocyclyl, 5- to 6-membered heterocyclyl, 5- to 6-membered heteroaryl, -L-A, -L-Het-L', -L-Het-A or
-L-A-Het-A, wherein L, L' and Het are as defined above and wherein each A is the same or different and is as defined above;
$R^6$ is hydrogen or $C_1$-$C_2$ alkyl;
$R^7$ is hydrogen or $C_1$-$C_2$ alkyl or $R^7$ is a $C_1$-$C_2$ alkyl moiety which is joined to one of the carbon atoms of B to form, together with the —N—C— moiety to which $R^7$ and B are attached, a pyrrolidine or piperidine ring; and
$R^8$ is hydrogen or $C_1$-$C_2$ alkyl;
wherein:
the alkyl, alkenyl and alkynyl groups and moieties in the substituents $R^1$ to $R^7$ and B are unsubstituted or substituted by a single hydroxy substituent or by one, two or three substituents which are the same or different and are selected from fluorine and chlorine substituents; and
the aryl, carbocyclyl, heterocyclyl and heteroaryl groups and moieties in the substituents $R^1$ and $R^5$, the heterocyclic or heteroaryl moieties formed by $R^1$ together with $R^2$ and $R^1$ together with $R^3$ and the heterocyclic moieties formed by $R^7$ together with B are typically unsubstituted or substituted by one, two or three substituents selected from fluorine, chlorine, hydroxy, $C_1$-$C_4$ alkyl, $C_1$-$C_4$ alkoxy and $C_1$-$C_4$ haloalkyl substituents.

Examples of such compounds are the more preferred compounds of formula (I) as defined above wherein:
A is phenyl or 5- to 6-membered heteroaryl; and $R^5$ is hydrogen, $C_1$-$C_6$ alkyl, phenyl, $C_3$-$C_6$ carbocyclyl, 5- to 6-membered heterocyclyl, 5- to 6-membered heteroaryl, -L-A, -L-Het-L' or -L-Het-A, wherein L, L', A and Het are as defined above.

Particularly preferred compounds of formula (I) are compounds of formula (II)

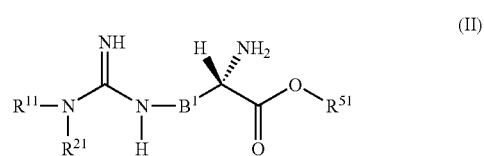

(II)

wherein:
either (a) $R^{11}$ is $C_3$-$C_8$ alkyl, allyl, phenyl, cyclopropyl, cyclohexyl, —($C_1$-$C_2$ alkyl)-phenyl, —($C_1$-$C_2$ alkyl)-thienyl, —($C_1$-$C_2$ alkyl)-tetrahydrofuranyl, —($C_1$-$C_2$ alkyl)-O-phenyl, —($C_1$-$C_2$ alkyl)-O—($C_1$-$C_4$ alkyl), —($C_1$-$C_2$ alkyl)-S—($C_1$-$C_2$ alkyl) or —($C_1$-$C_2$ alkyl)-NMe-($C_1$-$C_2$ alkyl);
$R^{21}$ is hydrogen, methyl or ethyl;
or (b) $R^{11}$ and $R^{21}$ form, together with the nitrogen to which they are attached, a piperidinyl, morpholinyl or pyrrolidinyl ring;
$B^1$ is a 1,2-ethyl or 1,3-propyl moiety; and
$R^{51}$ is hydrogen, $C_1$-$C_4$ alkyl, —($C_1$-$C_2$ alkyl)-phenyl, —($C_1$-$C_2$ alkyl)-O—($C_1$-$C_2$ alkyl) or —($C_1$-$C_2$ alkyl)-phenyl-O-phenyl;
wherein:
the alkyl groups and moieties in the substituents $R^{11}$, $R^{21}$, B and $R^{51}$ are unsubstituted or substituted by a single fluoro substituent; and
the phenyl and carbocyclyl groups in $R^{11}$ and the heterocyclic moieties formed by $R^{11}$ together with $R^{21}$ are unsubstituted and the phenyl groups in $R^{51}$ are unsubstituted or substituted by one or two substituents selected from fluorine, $C_1$-$C_2$ alkyl, $C_1$-$C_2$ alkoxy and $C_1$-$C_2$ haloalkyl substituents.

Examples of such compounds are the particularly preferred compounds of formula (II) as defined above wherein:
$R^{11}$ is $C_3$-$C_8$ alkyl, allyl, phenyl, cyclopropyl, cyclohexyl, —($C_1$-$C_2$ alkyl)-phenyl, —($C_1$-$C_2$ alkyl)-thienyl, —($C_1$-$C_2$ alkyl)-O-phenyl, —($C_1$-$C_2$ alkyl)-O—($C_1$-$C_4$ alkyl), —($C_1$-$C_2$ alkyl)-S—($C_1$-$C_2$ alkyl) or —($C_1$-$C_2$ alkyl)-NMe-($C_1$-$C_2$ alkyl); and
$R^{51}$ is hydrogen, $C_1$-$C_4$ alkyl or —($C_1$-$C_2$ alkyl)-phenyl, wherein:
the phenyl and carbocyclyl groups in $R^{11}$, the phenyl groups in $R^{51}$ and the heterocyclic moieties formed by $R^{11}$ together with $R^{21}$ are unsubstituted.

In one embodiment, $R^{11}$ is preferably phenyl, —($C_1$-$C_2$ alkyl)-phenyl, —($C_1$-$C_2$ alkyl)-thienyl, —($C_1$-$C_2$ alkyl)-tetrahydrofuranyl, —($C_1$-$C_2$ alkyl)-O-phenyl, —($C_1$-$C_2$ alkyl)-O—($C_1$-$C_4$ alkyl), —($C_1$-$C_2$ alkyl)-S—($C_1$-$C_2$ alkyl) or —($C_1$-$C_2$ alkyl)-NMe-($C_1$-$C_2$ alkyl). In a preferred embodiment of formula (II), $R^{11}$ is —($C_1$-$C_2$ alkyl)-O—($C_1$-$C_4$ alkyl). In a particularly preferred embodiment of formula (II), $R^{11}$ is —($CH_2$)$_2$—O—$CH_3$.

In a further preferred embodiment of formula (II), $R^{51}$ is $C_1$-$C_4$ alkyl or —($C_1$-$C_2$)-phenyl. In a particularly preferred embodiment of formula (II), $R^{51}$ is —$CH_2$-phenyl.

In a preferred embodiment of formula (II), $B^1$ is a 1,3-propyl moiety.

In a further preferred embodiment of formula (II), $R^{11}$ is —($C_1$-$C_2$ alkyl)-O—($C_1$-$C_4$ alkyl) and $R^{51}$ is $C_1$-$C_4$ alkyl or —(C₁-C₂)-phenyl. In a particularly preferred embodiment of formula (II), $R^{11}$ is —(C₁-C₂ alkyl)-O—(C₁-C₄ alkyl) and $R^{51}$ is C₁-C₄ alkyl.

Examples of these particularly preferred compounds of the invention are:

(S)-2-Amino-4-(N'-isopropylguanidino)butanoic acid;
(S)-2-Amino-4-(N'-propylguanidino)butanoic acid;
(S)-2-Amino-4-(N'-benzylguanidino)butanoic acid;
(S)-2-Amino-4-(N'-cyclohexylguanidino)butanoic acid;
(S)-2-Amino-4-(N'-phenylguanidino)butanoic acid;
(S)-2-Amino-4-(N'-(2-methoxyethyl)guanidino)butanoic acid;
(S)-2-Amino-4-(N'-(2-thiophenemethyl)guanidino)butanoic acid;
(S)-2-Amino-4-(N'-octylguanidino)butanoic acid;
(S)-2-Amino-4-(N'-cyclopropylguanidino)butanoic acid
(S)-2-Amino-4-(N'-(2'-dimethylaminoethyl)guanidino)butanoic acid;
(S)-2-Amino-4-(N'-2,2-dimethylpropyl)guanidino)butanoic acid;
(S)-2-Amino-4-(N'-(2-phenoxyethyl)guanidino)butanoic acid;
(S)-2-Amino-4-(N'-(2-methylthioethyl)guanidino)butanoic acid;
(S)-2-Amino-4-(N'-(2-isopropoxyethyl)guanidino)butanoic acid;
(S)-2-Amino-4-(N'-allylguanidino)butanoic acid;
(S)-2-Amino-4-[(piperidine-1-carboximidoyl)-amino]butanoic acid;
(S)-2-Amino-4-[(pyrrolidine-1-carboximidoyl)-amino]butanoic acid;
(S)-2-Amino-4-[(morpholine-4-carboximidoyl)-amino]butanoic acid;
(S)-4-(N'-(2-methoxyethyl)guanidino)pyrrolidine-2-carboxylic acid;
(S)-4-N'-(2-methoxyethyl)guanidinobutanoic acid;
$N^G$-(2-methoxyethyl)-L-arginine;
(S)-2-Amino-4-(N'-(2-methoxyethyl)guanidino)butanoic acid methyl ester;
(S)-2-Amino-4-(N'-(2-methoxyethyl)guanidino)butanoic acid ethyl ester;
(S)-2-Amino-4-(N'-(2-methoxyethyl)guanidino)butanoic acid propyl ester;
(S)-2-Amino-4-(N'-(2-methoxyethyl)guanidino)butanoic acid butyl ester;
(S)-2-Amino-4-(N'-(2-methoxyethyl)guanidino)butanoic acid benzyl ester;
(S)-2-Amino-4-(N'-(2-methoxyethyl)guanidino)butanoic acid isopropyl ester;
$N^G$-(2-Methoxyethyl)-L-arginine methyl ester;
$N^G$-(2-Methoxyethyl)-L-arginine benzyl ester;
(S)-2-Amino-5-(N'-(2-methoxyethyl)guanidino)pentanoic acid methylamide;
(S)-2-Amino-4-(N'-(2-methoxyethyl)guanidino)butanoic acid benzylamide;
(S)—$N^G$-((Tetrahydrofuran-2-yl)methyl)-arginine;
(2S)-2-Amino-4-$N^G$-((tetrahydrofuran-2-yl)methyl)guanidinobutanoic acid;
2-Methoxybenzyl (S)-2-amino-4-[(N'-(2-methoxyethyl)) guanidino]butanoate;
4-Methoxybenzyl (S)-2-amino-4-[(N'-(2-methoxyethyl)) guanidino]butanoate;
2-Fluorobenzyl (S)-2-amino-4-[(N'-(2-methoxyethyl)) guanidino]butanoate;
3-Trifluoromethyl-4-fluorobenzyl (S)-2-amino-4-[(N'-(2-methoxyethyl)) guanidino]butanoate;
3-Phenoxybenzyl (S)-2-amino-4-[(N'-(2-methoxyethyl)) guanidino]butanoate;
3-Methylbenzyl (S)-2-amino-4-[(N'-(2-methoxyethyl)) guanidino]butanoate;
3-Trifluoromethylbenzyl (S)-2-amino-4-[(N'-(2-methoxyethyl))guanidino]butanoate;
3-Fluorobenzyl (S)-2-amino-4-[(N'-(2-methoxyethyl)) guanidino]butanoate; and
2-Methoxyethyl (S)-2-amino-4-[(N'-(2-methoxyethyl)) guanidino]butanoate, and pharmaceutically acceptable salts thereof.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aralkyl amines or heterocyclic amines.

The compounds of the present invention have the chirality shown in formula (I). However, the compounds can also have chiral centres at other points in the molecule. For the avoidance of doubt, the chemical structures depicted herein are intended to embrace all stereoisomers of the compounds shown, provided they have the chirality at the carbon 0 to the carbonyl group which is shown in formula (I).

The compounds of formula (I) may be prepared by conventional routes, for example those set out in schemes 1 and 2 below.

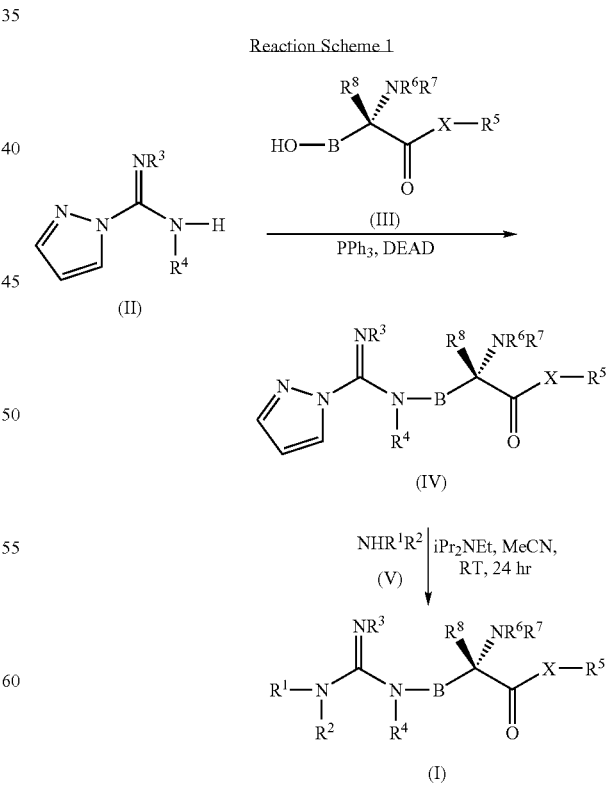

Compounds of formula (I) may be prepared from a substituted guanidine in a two step reaction as shown in Reaction Scheme 1, wherein $R^1$ to $R^8$, B and X are as defined above. In the first step, a substituent is introduced onto the carboxamide nitrogen by reaction with the appropriate alcohol under Mitsunobu conditions. In the second step a further substituent is introduced by displacement of the pyrazole moiety with a primary or secondary amine. Where necessary, when $R^2$, $R^3$, $R^5$ or $R^7$ are hydrogen, they can be replaced by a suitable protecting group which can then be removed after the second step. A suitable protecting group is Boc which can be removed under acid conditions, such as treatment with HCl in 1,4-doxane. The skilled person will readily understand when such protection is necessary. Compounds of formulae (II), (III) and (V) are known compounds or can be prepared by the skilled person using known methods. For example, compounds of formula (I) can be prepared from bis-tert-butoxycarbonylpyrazole-1-carboxamidine.

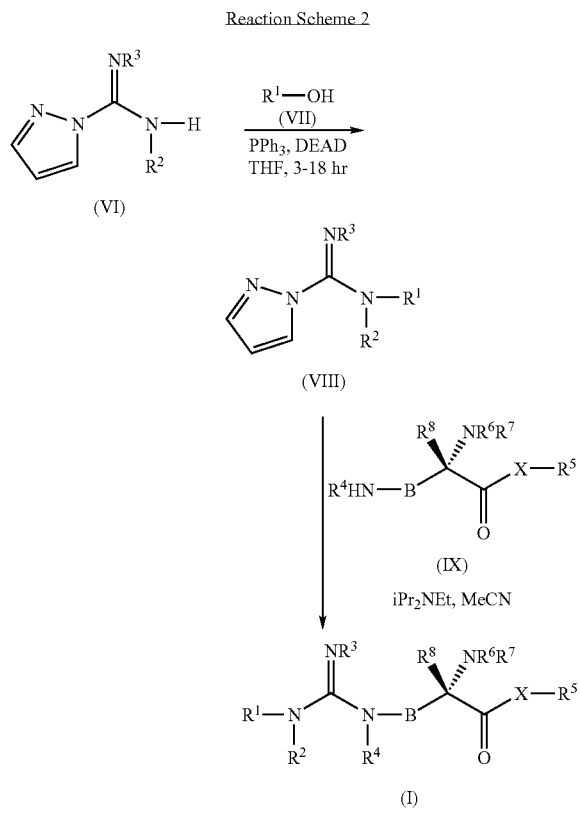

Reaction Scheme 2 is a variant of Reaction Scheme 1 and can be used to prepare compounds of formula (I) wherein $R^1$ is a primary or secondary alkyl group and $R^2$ to $R^8$, B and X are as defined above. Compounds of formulae (VI), (VII) and (IX) are known compounds or can be prepared by the skilled person using known methods. For example, compounds of formula (VI) can be prepared from bis-tert-butoxycarbonylpyrazole-1-carboxamidine.

The thus obtained compounds of formula (I) may be salified by treatment with an appropriate acid or base. Racemic mixtures obtained by any of the above processes can be resolved by standard techniques, for example elution on a chiral chromatography column.

An inhibitor of a DDAH is one which, when present, produces a measurable reduction in DDAH activity.

Preferred inhibitors are those which reduce DDAH activity by at least 10%, at least 20%, at least 30%, at least 40% at least 50%, at least 60%, at least 70%, at least 80%, at least 90%, at least 95% or at least 99% at a concentration of the inhibitor of 1 µg ml$^{-1}$, 10 µg ml$^{-1}$, 100 µg ml$^{-1}$, 500 µg ml$^{-1}$, 1 mg ml$^{-1}$, 10 mg ml$^{-1}$ or 100 mg ml$^{-1}$.

The percentage inhibition represents the percentage decrease in activity in a comparison of assays in the presence and absence of the test substance. Any combination of the above mentioned degrees of percentage inhibition or activation and concentration of inhibitor or activator may be used to define an inhibitor or activator of the invention, with greater inhibition at lower concentrations being preferred.

Inhibition may occur if, for example, the inhibitor resembles the substrate and binds at the active site of the DDAH. The substrate is thus prevented from binding to the same active site and the rate of catalysis is reduced by reducing the proportion of enzyme molecules bound to substrate (competitive inhibition). An inhibitor may also exert its effects by non-competitive inhibition where the inhibitor and substrate can bind simultaneously to DDAH and thus bind at different non-overlapping sites. Inhibition occurs as the turnover number of the DDAH decreases.

Typically, the compounds of the present invention cause substantially no inhibition of NOS expression or activity.

A suitable assay for inhibition of NOS activity is the [$^{14}$C] Arginine-[$^{14}$C] citrulline method which is described in D. S. Bredt and S. H. Snyder, Nitric oxide mediates glutamate-linked enhancement of cGMP levels in the cerebellum, Proc Natl Acad Sci USA, 1989 November, 86(22), 9030-3.

Typically, the compounds of the present invention achieve less than 50% inhibition, preferably less than 20% inhibition, more preferably less than 10% inhibition of NOS and particularly preferably less than 5% inhibition. In a preferred embodiment, the compounds of the present invention cause no detectable inhibition of NOS expression or activity. Generally, such results are achieved at a concentration of compound of 0.01 to 10 µm, for example 0.1 to 5, or 1 to 2 µm.

In one embodiment it is preferred that an inhibitor for use in the invention shows at least 100×, 1000× or at least 10$^6$× greater percentage inhibition of DDAH methylarginase activity and/or expression at a given concentration of inhibitor than the percentage inhibition of NOS at that same concentration.

In one embodiment, a compound of the invention has substantially no effect, activatory or inhibitory, upon NOS activity and/or substantially no effect upon NOS expression.

The compounds of the invention are found to be inhibitors of DDAH. The compounds of the present invention can therefore be used to treat a condition treatable by a DDAH inhibitor. The compounds of the invention are therefore therapeutically useful. Accordingly, the present invention provides a compound of the formula (I), as defined above, or a pharmaceutically acceptable salt thereof, for use in the treatment of the human or animal body. In particular, in the treatment of a condition in which the abnormal metabolism of NO is implicated. The present invention relates to the use of a compound of formula (I), as defined above, or a pharmaceutically acceptable salt thereof for use in the manufacture of a medicament for use in the treatment of a disease treatable by a DDAH inhibitor. In one embodiment, the present invention provides a compound of the formula (I), as defined above, or a pharmaceutically acceptable salt thereof, for use in the treatment of the human or animal body, provided that the compound of formula (I) N$^G$-propyl-L-arginine, N$^G$-allyl-L-arginine, N$^G$-propargyl-L-arginine, N$^G$-butyl-L-arginine or N$^G$-cyclopropyl-L-arginine. The compounds of the invention are believed to be novel and the present invention thus provides for compounds of formula (I), as defined above, or a pharmaceutically acceptable salt thereof. In one embodiment, the present invention provides a compound of formula (J), as defined above, or a pharmaceutically acceptable salt thereof provided that the compound of formula (I) is not propyl-L-arginine, e-allyl-L-arginine, $N^G$-propargyl-L-arginine, e-butyl-L-arginine or $N^G$-cyclopropyl-L-arginine. Also provided is a pharmaceutical composition comprising a compound of the formula (I), as defined above, or a pharmaceutically acceptable salt thereof, and a pharmaceutically acceptable carrier or diluent. In one embodiment, the present invention provides a pharmaceutical composition comprising a compound of the formula (I), as defined above, or a pharmaceutically acceptable salt thereof, and a pharmaceutically acceptable carrier or diluent, provided that the compound of formula (I) is not N-propyl-L-arginine, $N^G$-allyl-L-arginine, $N^G$-propargyl-L-arginine, $N^G$-butyl-L-arginine or $N^G$-cyclopropyl-L-arginine. Said pharmaceutical composition typically contains up to 85 wt % of a compound of the invention. More typically, it contains up to 50 wt % of a compound of the invention. Preferred pharmaceutical compositions are sterile and pyrogen free. Further, the pharmaceutical compositions provided by the invention typically contain a compound of the invention which is a substantially pure optical isomer.

As used herein, the term "disease whose pathology is affected by DDAH" refers to any disease wherein the level and/or activity of DDAH is not at the required amount to cause reversal of the pathology of the disease. In one embodiment, such diseases are associated with an increase in the expression of DDAH. Such diseases can be identified by measuring the expression of DDAH in a patient with a particular disease and comparing the results with a control. In another embodiment, a disease whose pathology is affected by DDAH is a disease wherein alteration in the level and/or activity of DDAH causes a change in the level and/or activity of another species which is associated with the disease. An example of such a species is NO. Such diseases can be identified by measuring the amount of this species in a patient before and after the administration of a compound of the present invention and determining whether there has been a change in the level and/or activity of said species.

The compounds of the invention may be administered in a variety of dosage forms. Thus, they can be administered orally, for example as tablets, troches, lozenges, aqueous or oily suspensions, dispersible powders or granules. Preferred pharmaceutical compositions of the invention are compositions suitable for oral administration, for example tablets and capsules.

Compositions suitable for oral administration may, if required, contain a colouring or flavoring agent. Typically, a said capsule or tablet comprises from 5 to 500 mg, preferably 10 to 500 mg, more preferably 15 to 100 mg, of a compound of formula (I) or a pharmaceutically acceptable salt thereof.

The compounds of the invention may also be administered parenterally, whether subcutaneously, intravenously, intramuscularly, intrasternally, transdermally or by infusion techniques. The compounds may also be administered as suppositories.

One preferred route of administration is inhalation. The major advantages of inhaled medications are their direct delivery to the area of rich blood supply in comparison to many medications taken by oral route. Thus, the absorption is very rapid as the alveoli have an enormous surface area and rich blood supply and first pass metabolism is bypassed.

Preferred pharmaceutical compositions of the invention therefore include those suitable for inhalation. The present invention also provides an inhalation device containing such a pharmaceutical composition. Typically said device is a metered dose inhaler (MDI), which contains a pharmaceutically acceptable chemical propellant to push the medication out of the inhaler. Typically, said propellant is a fluorocarbon.

Further preferred inhalation devices include nebulizers. Nebulizers are devices capable of delivering fine liquid mists of medication through a "mask" that fits over the nose and mouth, using air or oxygen under pressure. They are frequently used to treat those with asthma who cannot use an inhaler, including infants, young children and acutely ill patients of all ages.

Said inhalation device can also be, for example, a rotary inhaler or a dry powder inhaler, capable of delivering a compound of the invention without a propellant.

Typically, said inhalation device contains a spacer. A spacer is a device which enables individuals to inhale a greater amount of medication directly into the lower airways, where it is intended to go, rather than into the throat. Many spacers fit on the end of an inhaler; for some, the canister of medication fits into the device. Spacers with holding chambers and one-way valves prevent medication from escaping into the air. Many people, especially young children and the elderly, may have difficulties coordinating their inhalation with the action necessary to trigger a puff from a metered dose inhaler. For these patients, use of a spacer is particularly recommended.

Another preferred route of administration is intranasal administration. The nasal cavity's highly permeable tissue is very receptive to medication and absorbs it quickly and efficiently, more so than drugs in tablet form. Nasal drug delivery is less painful and invasive than injections, generating less anxiety among patients. Drugs can be delivered nasally in smaller doses than medication delivered in tablet form. By this method absorption is very rapid and first pass metabolism is bypassed, thus reducing inter-patient variability. Nasal delivery devices further allow medication to be administered in precise, metered doses. Thus, the pharmaceutical compositions of the invention are typically suitable for intranasal administration. Further, the present invention also provides an intranasal device containing such a pharmaceutical composition.

A further preferred route of administration is transdermal administration. The present invention therefore also provides a transdermal patch containing a compound of the invention, or a pharmaceutically acceptable salt thereof. Also preferred is sublingual administration. The present invention therefore also provides a sub-lingual tablet comprising a compound of the invention or a pharmaceutically acceptable salt thereof.

A compound of the invention is typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

A further preferred route of administration is intravenous administration. Solutions for injection or infusion may contain as carrier, for example, sterile water or preferably they may be in the form of sterile, aqueous, isotonic saline solutions. The compounds of the invention are inhibitors of DDAH and may be used in the treatment of conditions in which increased NO production is implicated. In particular, conditions such as ischaemia-reperfusion injury of the brain or heart, cancer, lethal hypotension in severe inflammatory conditions such as septic shock or multi-organ failure, or local and systemic inflammatory disorders including arthritis, skin disorders, inflammatory cardiac disease or migraine may be treated. Further, conditions such as neurodegeneration and asthma, wherein inhibition of NO has been suggested as a therapeutic option, can also be treated. The compounds of the invention can also be used in the treatment of ischaemia-reperfusion injury of the brain or heart, cancer, lethal hypotension in severe inflammatory conditions, local and systemic inflammatory disorders, neurodegeneration, asthma, pain or sepsis. The compounds of the present invention can further be used in the treatment of peritoneal inflammation. Preferably, the compounds of the present invention are used in the treatment of ischaemia-reperfusion injury of the brain or heart, cancer, lethal hypotension in severe inflammatory conditions, local and systemic inflammatory disorders, pain or sepsis.

Increased DDAH expression has also been implicated in an increase in tumour growth and angiogenesis (V. Kostourou, S. P. Robinson, J. E. Cartwright and G. St. J. Whitley, British Journal of Cancer 2002, 87, 673-680) and has been further implicated in enhanced tumour hypoxia (S. P. Robinson, V. Kostourou, H. Troy, J. F. Murray, G. Whitley and J. R. Griffiths, Clinical Cancer Research, 2003, 9, 6209s). DDAH overexpression has also been shown to enhance VEGF expression and the tube-forming capacity of cells. The compounds of the present invention can therefore be used in the treatment of conditions associated with tumour growth, angiogenesis and hypoxia and also enhanced VEGF expression. The compounds of the present invention can therefore be used for anti-angiogenic and anti-cancer therapy. In particular, the types of cancer that can be treated by the compounds of the present invention are those which are angiogenic in nature. The compounds of the present invention can further be used in the treatment of a tumour which overexpresses DDAH, for example DDAH1 overexpressing glioma (brain tumour) or pancreatic cancer.

The compounds of the present invention are thought to be particularly useful in the treatment of solid tumours. Examples of such solid tumours include ovarian cancer, colorectal cancer, breast cancer, brain cancer, liver cancer, kidney cancer, stomach cancer, prostate cancer, lung cancer, thyroid cancer, pancreatic cancer, Kaposis sarcoma and skin cancer. The compounds of the present invention are also thought to be useful in the treatment of head, neck and oesophageal solid tumours. Skin cancer is a preferred example a solid tumour for treatment by the compounds of the present invention and a preferred type of skin cancer is melanoma. A further preferred solid tumour for treatment by the compounds of the present invention is pancreatic cancer.

Inhibition of DDAH will result in an increase in the concentration of L-NMMA. L-NMMA has been shown to be effective in treating conditions such as inflammatory disease states, pain and sepsis. The compounds of the present invention can therefore be used in the treatment of such conditions.

Alternatively, the compounds of the present invention could be used as a joint therapy together with an inhibitor of NOS activity (for example, a methylarginine). For example, a specific inhibitor of a DDAH isoform could be used with the methylarginine L-NMMA. This approach may radically alter the activity profile of L-NMMA and may result in L-NMMA having an increased inhibitory effect for a specific NOS isoform. Thus, the invention provides products containing an inhibitor of a DDAH activity and/or expression and a methylarginine as a combined preparation for simultaneous, separate or sequential use in the treatment of ischaemia-reperfusion injury of the brain or heart, cancer, lethal hypotension in severe inflammatory conditions such as septic shock or multi-organ failure, or local and systemic inflammatory disorders including arthritis, skin disorders, inflammatory cardiac disease or migraine.

The compounds of the present invention are thought to be particularly suitable for acute clinical use.

The compounds of the present invention may also be used as antimicrobial agents, for example antibacterial agents. Therefore, the invention also provides a chemical entity for use in the treatment of a bacterial infection.

An inhibition in DDAH activity and/or expression has also been implicated in the treatment of inflammatory pain. A compound of the present invention is therefore useful for combating pain in a human or animal. An agent may act to alleviate existing pain in an individual or may be administered in anticipation of a painful condition. Thus treatment may be therapeutic or prophylactic. Preferably the compound is suitable for use in a mammal. In particular, it is preferred that the subject for treatment is human. However, the invention will also be of veterinary use for treating livestock and domestic animals. For example, the invention may be of use for treating cattle, pigs, sheep, horses, dogs, cats or rabbits.

Generally the pain to be treated is one in which pain signals are processed at least in part by the thalamus. For example, the pain may be "fast pain" for example, sharp pain, pricking pain, electric pain, or "slow pain", for example, burning pain, aching pain, throbbing pain, nauseous pain.

Attempts have been made to classify different types of pain. Among those classes which have been broadly identified, but which nevertheless overlap to an extent, are acute and chronic pain.

A definition of acute pain (Halpern (1984) *Advances in Pain Research and Therapy* Vol. 7, Ed. C. Bendetti et al, p 147) which is not intended to be limiting, is as a constellation of unpleasant sensory, perceptual and emotional experiences of certain associate autonomic (reflex) responses, and of psychological and behavioural reactions provoked by injury or disease. Tissue injury provokes a series of noxious stimuli which are transduced by nociceptors to impulses transmitted to the spinal cord and then to the upper part of the nervous system. Examples of acute pain are dental pain, post-operative pain, obstetric pain, headaches, neuralgia and myalgia.

A definition of chronic pain (Halpern (1984) ibid.) also not limiting, is pain that persists beyond the usual course of an acute disease or beyond a reasonable time for an injury to heal. Chronic pain is typically a result of persistent dysfunction of the nociceptive pain system. Examples of chronic pain include trigeminal neuralgia, post-herpetic neuralgia (a form of chronic pain accompanied by skin changes in a dermatomal distribution following damage by acute Herpes Zoster disease), diabetic neuropathy, causalgia, "phantom limb" pain and pain associated with osteoarthritis, rheumatoid arthritis and cancer. Some of these, for example, trigeminal neuralgia, diabetic neuropathic pain, causalgia, phantom limb pain and central post-stroke pain, have also been classified as neurogenic pain. One non-limiting definition of neurogenic pain is pain caused by dysfunction of the peripheral or central nervous system in the absence of nociceptor stimulation by trauma or disease.

Physiological and pathological pain have been defined in terms of their origin in the plasticity of the nervous system. The latter is defined in turn as the alteration in structure or function of the nervous system caused by development, experience or injury and can be either adaptive or maladaptive (Cervero, F. (1991) Eur. J. Neurosci Suppl 4, 162). Adaptive plasticity underlies the ability of the nervous system to compensate for damage or to produce changes in function which are appropriate to environmental change. Physiological pain, considered to be a sensation which reflects specific peripheral stimuli, is based on adaptive plasticity.

Maladaptive plasticity comprises those changes in the nervous system which lead to a disruption of function and therefore effectively constitute a disease state. Pathological pain is considered to be a sensation resulting from changes within the nervous system which bring about an alteration in the way in which information from the periphery, some of which is quite normal, is handled. Pathological pain is therefore based on maladaptive plasticity (Woolf, C. J. (1989) Br. J. Anaesth. 63, 139-146).

Maladaptive plasticity of the nociceptive system has also been shown, in experimental models, to be present in states of chronic pain. For instance, multiple injections of hyperalgesic substances such as $PGE_2$ into the paw of a rat have been shown to induce sustained hyperalgesia to mild pressure (e.g. Nakamura-Craig and Smith (1989) Pain 38, 91-98; Ferreira et al (1990) Pain 42, 365-371; Nakamura-Craig and Gill (1991) Neurosci. Lett. 124, 49-51).

A number of animal models have been developed of neuropathic pain in particular peripheral neuropathic pain, which suggest that this pain is often associated with partial denervation (Decosterd I and Woolf C J (2000) Pain 00:1-10). Such models mimic in particular, pain associated with, for example diabetic neuropathy, postherpetic neuralgia, toxic neuropathies, compression neuropathies and trauma, characterised by spontaneous lancinating, burning pain and shock like pain, as well as pain hypersensitivity including tactile allodynia, pinprick hyperalgesia and hyperpathia.

The compounds of the present invention can be used in a method of treating, including preventing, pain in a human or animal, the method comprising administering thereto a therapeutically or prophylactically effective amount of the agent. The compounds can be used in the therapeutic or prophylactic treatment of pathological conditions in which pain occurs. The condition of a human or animal to which the compound is administered can thereby be improved.

The compounds of the present invention are useful for treating or preventing different types of pain including chronic pain and acute pain. Examples of chronic pain which can be targeted using the present inhibitors include trigeminal neuralgia, post-herpetic neuralgia, painful diabetic neuropathy, causalgia, central post-stroke pain, "phantom limb" pain, atypical facial pain, back pain, headaches, neuralgia and pain associated with osteoarthritis, rheumatoid arthritis and cancer.

Examples of acute pain which can be treated using the compounds of the present invention include dental pain, post-operative pain, obstetric pain, headaches, neuralgia and myalgia. In particular, the compounds can be administered pre-operatively to counteract the acute pain associated with surgical operations, including dental surgery and labour pain. In a preferred embodiment the present invention comprises a method of administering a therapeutically effective amount of a compound to a patient prior to a dental operation, for example a tooth extraction. Virtually no analgesic agents currently in use are effective in controlling pain when administered pre-operatively in this way.

The invention also provides a method for treating pain according to which a compound of the present invention is administered jointly together with one or more other agents. For example, a compound may be administered with a known anti-pain agent. In one embodiment a compound of the present invention is administered with an inhibitor of NOS activity such as a methylarginine. For example, a compound of the present invention may be used in conjunction with L-NMMA and/or ADMA. This approach may radically alter the activity profile of L-NMMA and/or ADMA and may result in L-NMMA and/or ADMA having an increased inhibitory effect for NOS.

A compound of the present invention may be administered in parallel with another agent (such as methylarginine), or the agents may be administered sequentially, one following on from the other. Alternatively, a compound of the present invention and another agent (for example methylarginine), while acting together for the same purpose, may be administered separately. Thus, the invention provides products containing a compound of the present invention and a modulator of DDAH methylarginase activity and/or expression and a further agent (such as methylarginine) as a combined preparation for simultaneous, separate or sequential use in the treatment of pain in a human or animal.

As described, a compound of the present invention may be used to improve the condition of a patient experiencing pain or to prevent or reduce future pain. The formulation of a compound of the present invention for administration in preventing or alleviating pain will depend largely upon the nature of the compound. Formulation is also influenced, for example, by whether a pharmaceutical or veterinary use is intended, and by the requirement for passage across the blood-brain barrier. A compound may also be formulated for simultaneous, separate or sequential use with another substance such as a methylarginine. In general, it is preferred that the compound is directed or administered to neuronal cells, especially those of the CNS.

In one embodiment, the activity of the compounds of the invention is restricted only to particular cell types. For example, activity may be limited to neuronal cells especially those of the CNS, in particular thalamic cells. A compound may be formulated for uptake specifically by such cells. Alternatively, a compound of the present invention may be administered directly to such cells. For example, an agent may be injected into the thalamus.

The term treatment in this context is deemed to cover any effect from a cure of said condition to alleviation of any or all of the symptoms. The compounds of the invention may, where appropriate, be used prophylactically to reduce the incidence or severity of said conditions.

A therapeutically effective amount of a compound of the invention is administered to a patient. A typical dose is from about 0.001 to 50 mg per kg of body weight, for example 0.01 to 10 mg, according to the activity of the specific compound, the age, weight and conditions of the subject to be treated, the type and severity of the disease and the frequency and route of administration. Preferably, daily dosage levels are from 5 mg to 2 g. A daily dose may be given in one or more than one, for example, 2, 3 or 4 administrations.

The following Examples illustrate the invention. They do not, however, limit the invention in any way. In this regard, it is important to understand that the particular assays used in the Examples section are designed only to provide an indication of activity in inhibiting DDAH. A negative result in any one particular assay is not determinative.

EXAMPLES

General

All starting materials were either commercially available or reported previously in the literature unless noted. Solvents and reagents were used without further purification. Reactions were monitored by TLC on precoated silica gel plates (Kieselgel 60 $F_{254}$, Merck). Purification was performed by flash chromatography using silica gel (particle size 40-63 µM, Merck). $^1$H, and $^{13}$C NMR spectra were recorded on a Bruker AMX-300 or Bruker AMX-400 spectrometer. Chemical shifts are reported as ppm (δ) relative to TMS as an internal standard. Mass spectra were recorded on either a VG ZAB SE spectrometer (electron impact and FAB) or a Micromass Quattro electrospray LC-mass spectrometer. Melting points were determined on a Gallenkamp melting point apparatus and are uncorrected. Microanalaysis was carried out by the Analytical Services Section, University College London. All yields reported in the experimental section are non-optimized, isolated yields.

Method A: General Method for Synthesis of $N^G$-Monosubstituted Guanidine Amino Acids Diethyl azodicarboxylate (3 mmol) was added dropwise to a solution of N,N'-bis-tert-butoxycarbonylpyrazole-1-carboxamidine (2 mmol), triphenylphosphine (3 mmol) and the appropriate alcohol (2 mmol) at 0° C., with stirring. The mixture was then stirred at room temperature for 3-16 h, concentrated on the rotary evaporator and then subjected to flash column chromatography (10% ethyl acetate/cyclohexane) to give the product as a colourless oil.

The N-alkyl substituted pyrazolecarboxamidine (1.5 mmol), Boc-diaminoalkanoic acid tert-butyl ester (1.5 mmol) and diisopropylethylamine (2.0 mmol) were stirred in acetonitrile (10 mL) for 24 hours. The mixture was concentrated on the rotary evaporator, and then subjected to flash column chromatography (20-30% ethyl acetate/cyclohexane) to give the protected guanidino-amino acid as a colourless gum.

The protected amino acid was stirred in excess 4M hydrogen chloride/dioxane for 24-72 hours. Removal of solvent and byproducts in vacuo gave the amino acid as a white hygroscopic solid.

Method B: General Method for Synthesis of $N^G$-Disubstituted 2-amino-4-guanidinobutanoic Acids and $N^G$-Aryl 2-amino-4-guanidinobutanoic Acids Diethyl azodicarboxylate (3 mmol) was added dropwise to a solution of N,N'-bis-tert-butoxycarbonylpyrazole-1-carboxamidine (2 mmol), triphenylphosphine (3 mmol) and N-Boc-homoserine-tert-butyl ester (2 mmol) (prepared from the acid by the method described in Mathias, L. J. *Synthesis* 1979, 561-576) at 0° C., with stirring. The mixture was stirred at room temperature for 3-16 hours, concentrated on the rotary evaporator and then subjected to flash column chromatography (20% ethyl acetate/cyclohexane) to give the product as a colourless oil.

The N-substituted pyrazolecarboxamidine (1.5 mmol), was stirred with the appropriate secondary or aryl amine (1.5 mmol) in acetonitrile (10 mL) for 24 hours. The mixture was concentrated on the rotary evaporator, and then subjected to flash column chromatography (20-30% ethyl acetate/cyclohexane) to give the protected guanidino-amino acid as a colourless gum.

The protected amino acid was stirred in excess 4M hydrogen chloride/dioxane for 24-72 hours. Removal of solvent in vacuo gave the amino acid as a white hygroscopic solid.

Example 1

(S)-2-Amino-4-(N'-isopropylguanidino)butanoic acid

Yield 31% (Method A). $^1$H NMR (CD$_3$OD, 300 MHz): δ 4.00 (1H, t, J 6.5 Hz, CH), 3.67 (1H, septet, J 6.4 Hz, NCH(Me)$_2$), 3.43 (2H, t, J 6.9 Hz, CH$_2$), 2.21-2.03 (2H, m, CH$_2$), 1.16 (6H, d, J 6.4 Hz, (CH$_3$)$_2$); $^{13}$C NMR (75 MHz, CD$_3$OD, 27° C.) δ 171.6 (C), 157.1 (C), 51.9 (CH), 46.7 (CH), 39.4 (CH$_2$), 31.5 (CH$_2$), 23.1 (2×CH$_3$); MS (FAB+) found m/z 203.15101 (M+H), C$_8$H$_{18}$N$_4$O$_2$ M+H calc. 203.15709.

Example 2

(S)-2-Amino-4-(N'-propylguanidino)butanoic acid

Yield 35% (Method A). $^1$H NMR (CD$_3$OD, 300 MHz): δ 4.07 (1H, t, J 6.8 Hz, CH), 3.50 (2H, t, J 7.0 Hz, CH$_2$), 3.18 (2H, t, J 7.1 Hz, CH$_2$), 2.26-2.13 (2H, m, CH$_2$), 1.62 (2H, t, J 7.3, 7.1 Hz, CH$_2$), 0.98 (3H, t, J 7.3 Hz, CH$_3$); $^{13}$C NMR (75 MHz, CD$_3$OD, 27° C.) δ 171.6 (C), 158.0 (C), 51.8 (CH), 44.8 (CH$_2$), 39.4 (CH$_2$), 31.4 (CH$_2$), 23.6 (CH$_2$), 11.8 (CH$_3$); MS (FAB+) found m/z 202.14300 (M+H), C$_8$H$_{18}$N$_4$O$_2$ M+H calc. 202.14297.

Example 3

(S)-2-Amino-4-(N'-benzylguanidino)butanoic acid

Yield 55% (Method A). $^1$H NMR (CD$_3$OD, 300 MHz): δ 7.53-7.22 (5H, m, ArH), 4.59 (2H, s, PhCH$_2$), 4.15 (1H, t, J 6.7 Hz, CH), 3.66 (2H, t, J 7.2 Hz, CH$_2$), 2.41-2.24 (2H, m, CH$_2$); $^{13}$C NMR (75 MHz, CD$_3$OD, 27° C.) δ 171.5 (C), 158.0 (C), 137.9 (C), 130.3 (CH), 129.4 (CH), 128.8 (CH), 51.7 (CH), 46.5 (CH$_2$), 39.5 (CH$_2$), 31.4 (CH$_2$); MS (FAB+) found m/z 251.15045 (MH$^+$), C$_{12}$H$_{18}$N$_4$O$_2$ M+H calc. 251.15079.

Example 4

(S)-2-Amino-4-(N'-cyclohexylguanidino)butanoic acid

Yield 12% (Method A). $^1$H NMR (CD$_3$OD, 300 MHz): δ 3.99 (1H, t, J 6.2 Hz, CH), 3.43 (2H, t, J 6.8 Hz, CH$_2$), 2.21-2.06 (2H, m, CH$_2$), 1.87 (2H, br d, 2× cyclohexyl H), 1.72 (2H, br d, 2× cyclohexyl H), 1.55 (1H, m, NCH cyclohexyl), 1.41-1.14 (6H, m, 6× cyclohexyl H); $^{13}$C NMR (75 MHz, CD$_3$OD, 27° C.) δ 52.5 (CH), 52.0 (CH), 39.4 (CH$_2$), 34.2 (CH$_2$), 31.5 (CH$_2$), 26.6 (CH$_2$), 26.1 (CH$_2$); MS (FAB+) found m/z 243.18175 (M+H), C$_{11}$H$_{22}$N$_4$O$_2$ M+H calc. 243.18209.

Example 5

(S)-2-Amino-4-(N'-phenylguanidino)butanoic acid

Yield 17% (Method B). $^1$H NMR (CD$_3$OD, 300 MHz): δ 7.47 (2H, t, J 7.3 Hz Ar C2H, C5H), 7.37 (1H, t, J7.3 Hz, Ar C4H), 7.31 (2H, m, Ar C3H, C5H), 4.10 (1H, t, J6.3 Hz, CH), 3.59 (2H, t, J 7.0 Hz, CH$_2$), 2.33-2.14 (2H, m, CH$_2$); $^{13}$C NMR (75 MHz, CD$_3$OD, 27° C.) δ 171.5 (C), 131.5 (CH), 129.2 (CH), 127.1 (CH), 51.9 (CH), 39.8 (CH$_2$), 31.4 (CH$_2$); MS (FAB+) found m/z 237.13543 (M+H), C$_{11}$H$_{16}$N$_4$O$_2$ M+H calc. 237.13514.

Example 6

(S)-2-Amino-4-(N'-(2-methoxyethyl)guanidino)butanoic acid

Yield 41% (Method A). $^1$H NMR (CD$_3$OD, 300 MHz): δ 4.29 (1H, t, J 6.7 Hz, CH), 3.78-3.68 (4H, m, 2×CH$_2$), 3.63 (2H, m, OCH$_2$), 3.61 (3H, s, OCH$_3$), 2.51-2.33 (2H, m, CH$_2$); $^{13}$C NMR (75 MHz, CD$_3$OD, 27° C.) δ 171.6 (C), 158.0 (C), 72.6 (CH$_2$), 59.6 (CH$_3$), 51.8 (CH), 43.5 (CH$_2$), 39.5 (CH$_2$), 31.4 (CH$_2$); MS (FAB+) found m/z 219.14585 (M+H), C$_8$H$_{18}$N$_4$O$_3$ M+H calc. 219.14585.

Example 7

(S)-2-Amino-4-(N'-octylguanidino)butanoic acid

Yield 18% (Method A). $^1$H NMR (CD$_3$OD, 300 MHz): δ 4.13 (1H, t, J 6.5 Hz, CH), 3.56 (2H, t, J 6.7 Hz, NCH$_2$), 3.28 (2H, t, J=7.1 Hz, NCH$_2$), 2.37-2.17 (2H, m, CH$_2$), 1.42-1.38 (10H, m, 5×CH$_2$), 0.97 (3H, m, CH$_3$); $^{13}$C NMR (75 MHz, CD$_3$OD, 27° C.) δ; MS (FAB+), found m/z 273.22849 (M+H), C$_{13}$H$_{28}$N$_4$O$_2$ M+H calc. 273.22903.

Example 8

(S)-2-Amino-4-(N'-cyclopropylguanidino)butanoic acid

Yield 41% (Method B). $^1$H NMR (CD$_3$OD, 300 MHz): δ 4.07 (1H, t, J 6.5 Hz, CH), 3.50 (2H, t, J 6.9 Hz, CH$_2$), 2.52 (1H, m, NCH cyclopropyl), 2.27-2.11 (2H, br m, CH$_2$), 0.89 (2H, m, 2×CH cyclopropyl), 0.66 (2H, m, 2×CH cyclopropyl); $^{13}$C NMR (75 MHz, CD$_3$OD, 27° C.) δ 171.6 (C), 159.3 (C), 51.9 (CH), 39.4 (CH$_2$), 31.4 (CH$_2$), 23.9 (CH), 8.2 (CH$_2$); MS (FAB+) found m/z 201.13519 (M+H), C$_8$H$_{16}$N$_4$O$_2$ M+H calc. 201.13514.

Example 9

(S)-2-Amino-4-(N'-(2'-dimethylaminoethyl)guanidino)butanoic acid

Yield 0.29% (Method B). $^1$H NMR (CD$_3$OD, 300 MHz): δ 4.15 (1H, t, J 6.7 Hz, CH), 3.73 (2H, t, J 6.2 Hz, NCH$_2$), 3.56 (2H, t, J 7.1 Hz, NCH$_2$), 3.43 (2H, t, J 6.2 Hz, NCH$_2$), 2.96 (6H, s, N(CH$_3$)$_2$), 2.32-2.19 (2H, m, CH$_2$); $^{13}$C NMR (75 MHz, CD$_3$OD, 27° C.) δ 171.2 (C), 158.0 (C), 56.9 (CH$_2$), 51.4 (CH), 43.9 (CH$_3$), 39.2 (CH$_2$), 37.9 (CH$_2$), 30.8 (CH$_2$); MS (FAB+), found m/z 232.17283 (M+H), C$_9$H$_{21}$N$_5$O$_2$ M+H calc 232.17734.

Example 10

(S)-2-Amino-4-(N'-2,2-dimethylpropyl)guanidino)butanoic acid

Yield 18% (Method A). $^1$H NMR (CD$_3$OD, 300 MHz): δ 4.18 (1H, t, J 6.7 Hz, CH), 3.62 (2H, t, J 7.3 Hz, CH$_2$), 3.14 (2H, s, NCH$_2$(Me)$_3$), 2.40-2.21 (2H, m, CH$_2$), 1.09 (9H, s, (CH$_3$)$_3$); $^{13}$C NMR (75 MHz, CD$_3$OD, 27° C.) δ 171.5 (C), 158.0 (C), 54.2 (CH$_2$), 51.8 (CH$_2$), 39.5 (CH$_2$), 33.5 (C), 31.5 (CH$_2$), 27.7 (3×CH$_3$); MS (FAB+) found m/z 231.18222 (M+H), C$_{10}$H$_{22}$N$_4$O$_2$ M+H calc. 231.18209.

Example 11

(S)-2-Amino-4-(N'-(2-phenoxyethyl)guanidino)butanoic acid

Yield 56% (Method A). $^1$H NMR (CD$_3$OD, 300 MHz): δ 7.31-7.24 (2H, m, 2×ArH), 6.97-6.92 (3H, m, 3×ArH), 4.14 (2H, t, J 5.1 Hz, CH$_2$), 4.09 (1H, t, J 6.9 Hz, CH), 3.66 (2H, t, J 5.1 Hz, CH$_2$), 3.52 (2H, t, J 7.1 Hz, CH$_2$), 2.30-2.12 (2H, m, CH$_2$); $^{13}$C NMR (75 MHz, CD$_3$OD, 27° C.) δ 171.2 (C), 159.8 (C), 158.0 (C), 130.6 (CH), 122.4 (CH), 115.6 (CH), 67.4 (CH$_2$), 51.4 (CH), 42.5 (CH$_2$), 39.1 (CH$_2$), 30.9 (CH$_2$); MS (FAB+) found m/z 281.16180 (M+H), C$_{13}$H$_{20}$N$_4$O$_3$ M+H calc. 281.16136.

Example 12

(S)-2-Amino-4-(N'-(2-methylthioethyl)guanidino)butanoic acid

Yield 38% (Method A). $^1$H NMR (CD$_3$OD, 300 MHz): δ 4.09 (1H, t, J 6.6 Hz, CH), 3.51 (2H, t, J 7.1 Hz, CH$_2$), 3.46 (2H, t, J 6.7 Hz, CH$_2$), 2.72 (2H, t, J 6.7 Hz, SCH$_2$), 2.30-2.12 (2H, m, CH$_2$), 2.13 (3H, s, SCH$_3$); $^{13}$C NMR (75 MHz, CD$_3$OD, 27° C.) δ 171.2 (C), 157.6 (C), 51.4 (CH), 41.8 (CH$_2$), 39.0 (CH$_2$), 33.9 (CH$_2$), 30.9 (CH$_2$), 15.2 (CH$_3$); MS (FAB+) found m/z 235.12235 (M+H), C$_8$H$_{18}$N$_4$O$_2$S M+H calc. 235.12287.

Example 13

(S)-2-Amino-4-(N'-(2-isopropoxyethyl)guanidino)butanoic acid

Yield 41% (Method A). $^1$H NMR (CD$_3$OD, 300 MHz): δ 4.08 (1H, t, J 6.5 Hz, CH), 3.65 (1H, septet, J 6.1 Hz, OCH), 3.59 (2H, t, J 5.1 Hz, CH$_2$), 3.50 (2H, t, J 7.1 Hz, CH$_2$), 3.39 (2H, t, J 5.1 Hz, CH$_2$), 2.30-2.11 (2H, m, CH$_2$), 1.17 (5H, d, J 6.1 Hz, 2×CH$_3$); $^{13}$C NMR (75 MHz, CD$_3$OD, 27° C.) δ 171.2 (C), 158.4 (C), 73.7 (CH), 51.4 (CH), 43.6 (CH$_2$), 39.1 (CH$_2$), 31.0 (CH$_2$), 22.3 (CH$_3$); MS (FAB+) found m/z 247.17699 (M+H), C$_{10}$H$_{22}$N$_4$O$_3$ M+H calc. 247.17701.

Example 14

(S)-2-Amino-4-(N'-allylguanidino)butanoic acid

Yield 50% (Method A). $^1$H NMR (CD$_3$OD, 300 MHz): δ 5.99-5.87 (1H, m, vinyl CH), 5.34 (1H, d, J 17.1 Hz, cis vinyl CH), 5.27 (1H, d, J 10.4 Hz, trans vinyl CH), 4.13 (1H, t, J 6.6

Hz, NCH), 3.93 (2H, d, J 4.9 Hz. NCH$_2$), 3.57 (2H, t, J 6.0 Hz, CH$_2$), 2.37-2.15 (2H, m, CH$_2$); $^{13}$C NMR (75 MHz, CD$_3$OD, 27° C.) δ 171.5 (C), 158.0 (C), 134.1 (CH), 117.9 (CH$_2$), 51.8 (CH), 45.0 (CH$_2$), 39.4 (CH$_2$), 35.2 (CH$_2$), 31.4 (CH$_2$); MS (FAB+) found m/z 201.13558 (M+H), C$_8$H$_{16}$N$_4$O$_2$ M+H calc. 201.13514.

Example 15

(S)-2-Amino-4-[(piperidine-1-carboximidoyl)-amino]butanoic acid

Yield 32% (Method B). $^1$H NMR (CD$_3$OD, 300 MHz): δ 4.08 (1H, t, J 6.5 Hz, NCH), 3.54 (2H, t, J7.1 Hz, CH$_2$), 3.48-3.44 (4H, m, 2×CH$_2$), 2.31-2.13 (2H, m, CH$_2$), 1.68-1.59 (6H, m, 3×CH$_2$); $^{13}$C NMR (75 MHz, CD$_3$OD, 27° C.) δ 171.7 (C), 157.5 (C), 51.9 (CH), 40.3 (CH$_2$), 31.3 (CH$_2$), 26.9 (CH$_2$), 25.2 (CH$_2$); MS (FAB+) found m/z 229.16582 (M+H), C$_{10}$H$_{20}$N$_4$O$_2$ M+H calc. 229.16644.

Example 16

(S)-2-Amino-4-[(pyrrolidine-1-carboximidoyl)-amino]butanoic acid

Yield 23% (Method B). $^1$H NMR (CD$_3$OD, 300 MHz): δ 4.11 (1H, t, J 6.2 Hz, CH), 3.54 (2H, t, J 6.8 Hz, CH$_2$), 3.44 (4H, t, J 6.4 Hz, 2×NCH$_2$ pyrr), 2.32-2.05 (2H, m, CH$_2$), 2.03 (4H, t, J 6.4 Hz, 2×CH$_2$); $^{13}$C NMR (75 MHz, CD$_3$OD, 27° C.) δ 171.4 (C), 155.0 (C), 51.5 (CH), 48.5 (CH$_2$), 39.4 (CH$_2$), 30.9 (CH$_2$), 26.2 (CH$_2$); MS (FAB+) found m/z 215.15070 (M+H), C$_9$H$_{18}$N$_4$O$_2$ M+H calc. 215.15079.

Example 17

(S)-2-Amino-4-[(morpholine-4-carboximidoyl)-amino]butanoic acid

Yield 30% (Method B). $^1$H NMR (CD$_3$OD, 300 MHz): δ 4.09 (1H, t, J 6.2 Hz, CH), 3.74 (4H, t, J 4.9 Hz, 2×CH$_2$ morph), 3.55 (2H, t, J 6.8 Hz, CH$_2$), 3.48 (4H, t, J 4.9 Hz, 2×CH$_2$ morph), 2.30-2.19 (2H, m, CH$_2$); $^{13}$C NMR (75 MHz, CD$_3$OD, 27° C.) δ 66.9 (CH$_2$), 51.5 (CH), 47.6 (CH$_2$), 39.9 (CH$_2$), 30.8 (CH$_2$); MS (FAB+) found m/z 231.14593 (M+H), C$_9$H$_{18}$N$_4$O$_3$ M+H calc. 231.14571.

Example 18

(S)-4-(N'-methylguanidino)pyrrolidine-2-carboxylic acid

Yield 38% (Method B, from N-Boc-Hydroxyproline-OBu$^t$). $^1$H NMR (CD$_3$OD, 300 MHz): δ 4.55-4.43 (2H, m, CH$_2$), 3.77-3.68 (1H, m, CH), 3.44-3.31 (1H, m, CH), 2.94-2.84 (1H, m, CH) 2.87 (3H, s, CH$_3$), 2.27-2.17 (1H, m, CH); $^{13}$C NMR (75 MHz, CD$_3$OD, 27° C.) δ; 170.4 (C), 158 (C), 59.6 (CH$_2$), 51.6 (CH$_1$) 50.6 (CH$_2$), 35.2 (CH$_2$), 28.6 (CH$_3$); MS (FAB+) found m/z 187.10587 (M+H), C$_7$H$_{14}$N$_4$O$_2$ M+H calc. 187.11950.

Example 19

(S)-4-(N'-(2-methoxyethyl)guanidino)pyrrolidine-2-carboxylic acid

Yield 26% (Method B, from N-Boc-Hydroxyproline-OBu$^t$). $^1$H NMR (CD$_3$OD, 300 MHz): δ 4.55-4.45 (2H, m, CH$_2$), 3.75-3.71 (1H, m, CH), 3.54 (2H, t, J 4.8 Hz, CH$_2$), 3.44-3.40 (3H, m, CH$_2$+CH), 3.38 (3H, s, OCH$_3$), 2.89-2.85 (1H, m, CH), 2.28-2.21 (1H, m, CH); $^{13}$C NMR (75 MHz, CD$_3$OD, 27° C.) δ 170.4 (C), 159.0 (C), 72.1 (CH$_2$), 59.6 (CH), 59.2 (CH$_3$), 51.7 (CH), 50.7 (CH$_2$), 43.2 (CH$_2$), 35.2 (CH$_2$); MS (FAB+) found m/z 231.14592 (M+H), C$_9$H$_{18}$N$_4$O$_3$ M+H calc. 231.14571.

Example 20

(S)-4-N'-(2-methoxyethyl)guanidinobutanoic acid

Yield 59% (Method A, from 4-amino-tert-butylbutanoate). $^1$H NMR (CD$_3$OD, 300 MHz): δ 3.53 (2H, t, J 4.7 Hz, CH$_2$), 3.39-3.34 (2H, m, CH$_2$), 3.36 (3H, s, OCH$_3$), 3.24 (2H, t, J 7.1 Hz, CH$_2$), 2.39 (2H, t, J 7.1 Hz, CH$_2$), 1.86 (2H, quintet, J 7.1 Hz, CH$_2$); $^{13}$C NMR (75 MHz, CD$_3$OD, 27° C.) δ 176.7 (C), 158.0 (C), 72.7 (CH$_2$), 59.2 (CH$_3$), 42.9 (CH$_2$), 41.9 (CH$_2$), 31.5 (CH$_2$), 25.2 (CH$_2$); MS (FAB+) found m/z 204.13477 (M+H), C$_8$H$_{17}$N$_3$O$_3$ M+H calc. 204.13481.

Example 21

N$^G$-(2-methoxyethyl)-L-arginine

Yield 44% (Method A, from Boc-Orn-OBu$^t$). $^1$H NMR (CD$_3$OD, 300 MHz): δ 4.03 (1H, t, J 6.0 Hz, CH), 3.53 (2H, t, J 5.0 Hz, CH$_2$), 3.39 (2H, t, J 5.0 Hz, CH$_2$), 3.37 (3H, s, OCH$_3$), 3.30 (2H, m, CH$_2$), 2.03-1.94 (2H, m, CH$_2$), 1.83-1.72 (2H, m, CH$_2$); $^{13}$C NMR (75 MHz, CD$_3$OD, 27° C.) δ 171.5 (C), 158.2 (C), 72.2 (CH$_2$), 59.2 (CH$_3$), 53.5 (CH), 42.9 (CH$_2$), 41.9 (CH$_2$), 28.7 (CH$_2$), 25.8 (CH$_2$); MS (FAB+) found m/z 233.16097 (M+H), C$_9$H$_{20}$N$_4$O$_3$ M+H calc. 233.16136.

General Method for Preparation of Esters

To a solution of the acid (typically 0.5 mmol) in the appropriate alcohol (2 mL) at 0° C. was added thionyl chloride (1.1 equivalents), with stirring. The solution was stirred for 30 minutes at 0° C. and then heated under reflux for 1 hour and stirred at room temperature overnight. Solvent was then removed in vacuo to give the ester as a white or yellow solid.

Example 22

(S)-2-Amino-4-(N'-(2-methoxyethyl)guanidino)butanoic acid methyl ester

Yield 83%. $^1$H NMR (CD$_3$OD, 300 MHz): δ 4.15 (1H, t, J 6.5 Hz, CH), 3.86 (3H, s, OCH$_3$), 3.54 (2H, t, J 4.9 Hz, CH$_2$), 3.47 (2H, t, J 7.1 Hz, CH$_2$), 3.42 (2H, t, J 6.0 Hz, CH$_2$), 3.38 (3H, s, OCH$_3$), 2.29-2.11 (2H, m, CH$_2$); $^{13}$C NMR (75 MHz, CD$_3$OD, 27° C.) δ 170.3 (C), 157.5 (C), 72.1 (CH$_2$), 59.2 (CH$_3$), 54.0 (CH$_3$), 51.5 (CH), 43.0 (CH$_2$), 38.8 (CH$_2$), 30.9 (CH$_2$); MS (FAB+) found m/z 233.16097 (M+H), C$_9$H$_{20}$N$_4$O$_3$ M+H calc. 233.16136.

Example 23

(S)-2-Amino-4-(N'-(2-methoxyethyl)guanidino)butanoic acid ethyl ester

Yield 84%. $^1$H NMR (CD$_3$OD, 300 MHz): δ 4.33 (2H, q, J 7.1 Hz, CH$_2$), 4.13 (1H, t, J 6.2 Hz, CH), 3.55-3.39 (6H, m, 3×CH$_2$), 3.38 (3H, s, OCH$_3$), 2.28-2.20 (2H, m, CH$_2$), 1.34 (3H, t, J 7.1 Hz, CH$_3$); $^{13}$C NMR (75 MHz, CD$_3$OD, 27° C.) δ 169.9 (C), 158.3 (C), 72.1 (CH$_2$), 64.1 (CH$_2$), 59.2 (CH$_3$), 51.5 (CH), 43.1 (CH$_2$), 38.9 (CH$_2$), 30.9 (CH$_2$), 14.4 (CH$_3$); MS (FAB+) found m/z 247.17723 (M+H), C$_{10}$H$_{22}$N$_4$O$_3$ M+H calc. 247.17701.

Example 24

(S)-2-Amino-4-(N-(2-methoxyethyl)guanidino)butanoic acid propyl ester

Yield 80%. $^1$H NMR (CD$_3$OD, 300 MHz): δ 4.25-4.15 (3H, m, CH, CH$_2$), 3.56-3.39 (6H, m, 3×CH$_2$), 3.38 (3H, s, OCH$_3$), 2.27-2.15 (2H, m, CH$_2$), 1.73 (2H, m, CH$_2$), 0.98 (3H, t, J 7.1 Hz, CH$_3$); $^{13}$C NMR (75 MHz, CD$_3$OD, 27° C.) δ 170.0 (C), 158.1 (C), 72.1 (CH$_2$), 69.5 (CH$_2$), 59.3 (CH$_3$), 51.6 (CH), 43.1 (CH$_2$), 38.9 (CH$_2$), 30.9 (CH$_2$), 22.9 (CH$_2$), 10.7 (CH$_3$); MS (FAB+) found m/z 261.19258 (M+H), C$_{11}$H$_{24}$N$_4$O$_3$ M+H calc. 261.19266.

Example 25

(S)-2-Amino-4-(N'-(2-methoxyethyl)guanidino)butanoic acid butyl ester

Yield 60%. $^1$H NMR (CD$_3$OD, 300 MHz): δ; $^{13}$C NMR (75 MHz, CD$_3$OD, 27° C.)$_6$; MS (FAB+) found m/z 275.20818 (M+H), C$_{12}$H$_{26}$N$_4$O$_3$ M+H calc. 275.20831.

Example 26

(S)-2-Amino-4-(N'-(2-methoxyethyl)guanidino)butanoic acid benzyl ester

Yield 79%. $^1$H NMR (CD$_3$OD, 300 MHz): δ 7.45-7.27 (5H, m, ArH), 5.23 (2H, s, PhCH$_2$O), 4.20 (1H, t, J 6.2 Hz, CH), 3.59-3.42 (6H, m, 3×CH$_2$), 3.30 (3H, s, OCH$_3$), 2.27-2.11 (2H, m, CH$_2$); $^{13}$C NMR (75 MHz, CD$_3$OD, 27° C.) δ 169.9 (C), 158.0 (C), 136.3 (C), 129.9 (CH), 129.4 (CH), 129.0 (CH), 72.1 (CH$_2$), 69.5 (CH$_2$), 59.2 (CH$_3$), 51.6 (CH), 43.0 (CH$_2$), 38.9 (CH$_2$), 30.9 (CH$_2$); MS (FAB+) found m/z 309.19466 (M+H), C$_{15}$H$_{24}$N$_4$O$_3$ M+H calc. 309.19266.

Example 27

(S)-2-Amino-4-(N'-(2-methoxyethyl)guanidino)butanoic acid isopropyl ester

Yield 72%. $^1$H NMR (CD$_3$OD, 300 MHz): δ 5.11 (1H, septet, J 6.2 Hz, (Me)$_2$CH), 4.12 (1H, t, J 6.7 Hz, CH), 3.56-3.42 (6H; m, 3×CH$_2$), 3.38 (3H, s, OCH$_3$), 2.29-2.04 (2H, m, CH$_2$), 1.33 (6H, d, J 6.2 Hz, (CH$_3$)$_2$); $^{13}$C NMR (75 MHz, CD$_3$OD, 27° C.) δ 169.5 (C), 158.1 (C), 72.5 (CH$_2$), 72.1 (CH) 59.3 (CH$_3$), 51.6 (CH), 43.1 (CH$_2$), 39.0 (CH$_2$), 31.0 (CH$_2$), 21.9 (CH$_3$); MS (FAB+) found m/z 261.19378 (M+H), C$_{11}$H$_{24}$N$_4$O$_3$ M+H calc. 261.19266.

Example 28

N$^G$-(2-Methoxyethyl)-L-arginine methyl ester

Yield 80%. $^1$H NMR (CD$_3$OD, 300 MHz): δ 4.12 (1H, t, J 6.0 Hz, CH), 3.85 (3H, s, OCH$_3$), 3.53 (2H, t, J 4.7 Hz, CH$_2$), 3.40 (2H, t, J 4.7 Hz, CH$_2$), 3.38 (3H, s, OCH$_3$), 3.31-3.27 (2H, m, CH$_2$), 2.10-1.92 (2H, m, CH$_2$), 1.84-1.69 (2H, m, CH$_2$); $^{13}$C NMR (75 MHz, CD$_3$OD, 27° C.) δ 170.7 (C), 158.1 (C), 72.2 (CH$_2$), 59.3 (CH$_3$), 53.9 (CH$_3$), 53.6 (CH), 43.0 (CH$_2$), 41.9 (CH$_2$), 28.7 (CH$_2$), 25.8 (CH$_2$); MS (FAB+) found m/z 247.17725 (M+H), C$_{10}$H$_{22}$N$_4$O$_3$ M+H calc. 247.17701.

General Method for Preparation of Amides

Amine derivatives of the guanidine amino acids can be synthesised using a modified version of Method A. For example, 3-N'-(2-methoxyethyl)guanidinopropylamine can be synthesized from Method A using Boc-1,3-diaminopropane.

Preparative Example 1

3-N$^G$-(2-Methoxyethyl)guanidinopropylamine

Yield 63% (Method A, from Boc-1,3-diaminopropane). $^1$H NMR (CD$_3$OD, 300 MHz): δ 3.53 (2H, t, J 5.0 Hz, CH$_2$), 3.40 (2H, t, J 5.0 Hz, CH$_2$), 3.38 (3H, s, OCH$_3$), 3.34 (2H, t, J 7.0 Hz, CH$_2$), 3.02 (2H, t, J 7.6 Hz, CH$_2$), 1.96 (2H, tt, J 7.0, 7.6 Hz, CH$_2$); $^{13}$C NMR (75 MHz, CD$_3$OD, 27° C.) δ 158.2 (C), 72.2 (CH$_2$), 59.2 (CH$_3$), 43.0 (CH$_2$), 39.7 (CH$_2$), 38.2 (CH$_2$), 28.0 (CH$_2$); MS (FAB+) found m/z 175.15591 (M+H), C$_7$H$_{18}$N$_4$O M+H calc. 175.15588.

Isobutyl chloroformate (1 mmol) and N-methylmorpholine (1 mmol) were added to L-Boc-ornithine(Fmoc) (1 mmol) in chloroform (5 mL) at −10° C., with stirring. The mixture was stirred at −10° C. for 15 minutes, and then the required amine (1 mmol) was added and the mixture stirred for a further 3 hours with gradual warming to room temperature. The solvent was removed in vacuo and the residue subjected to flash column chromatography (1:1 cyclohexane: ethyl acetate) to give the amide as a white powder.

The amide (0.5 mmol) was stirred with piperidine (5 equivalents) in chloroform (3 mL) with monitoring by tlc until the starting material was consumed. Solvent and excess piperidine were removed in vacuo and the entire crude product was used in the next step.

The N-alkyl substituted pyrazolecarboxamidine (0.5 mmol), and the crude Boc-protected amide (~0.5 mmol) were stirred in acetonitrile (5 mL) for 48 hours. After removal of solvent, the residue was subjected to flash column chromatography to give the Boc-protected guanidino-amino amide.

The Boc-protected amide was stirred in excess HCl/dioxane for 72 hours, then the solvent removed in vacuo to give the product as a white solid.

Example 29

(S)-2-Amino-5-(N'-(2-methoxyethyl)guanidino)pentanoic acid methyl amide

Yield 36%. $^1$H NMR (CD$_3$OD, 300 MHz): δ 3.92 (1H, t, J 6.5 Hz, CH), 3.53 (2H, t, J 4.7 Hz, CH$_2$), 3.40 (2H, t, J 5.0 Hz, CH$_2$), 3.37 (3H, s, NCH$_3$), 3.32-3.26 (2H, m, CH$_2$), 2.79 (3H, s, CH$_3$), 1.96-1.89 (2H, m, CH$_2$), 1.74-1.66 (2H, m, CH$_2$); $^{13}$C NMR (75 MHz, CD$_3$OD, 27° C.) δ 170.3 (C), 158.1 (C), 72.2 (CH$_2$), 59.3 (CH$_3$), 54.1 (CH), 43.0 (CH$_2$), 42.0 (CH$_2$), 29.7 (CH$_2$), 26.4 (CH$_3$), 25.6 (CH$_2$); MS (FAB+) found m/z 246.19305 (M+H), C$_{10}$H$_{23}$N$_5$O$_2$ M+H calc. 246.19299.

Example 30

(S)-2-Amino-4-(N'-(2-methoxyethyl)guanidino)butanoic acid benzylamide

Yield 33%. $^1$H NMR (CD$_3$OD, 300 MHz): 7.33-7.22 (5H, m, ArH), 4.43 (2H, d, J 5.5 Hz, CH$_2$), 4.09 (1H, t, J 6.7 Hz, CH), 3.53-3.40 (4H, m, 2×CH$_2$), 3.36 (3H, s, OMe), 2.24-

2.09 (2H, m, CH$_2$); $^{13}$C NMR (75 MHz, CD$_3$OD, 27° C.) δ 169.9 (C), 158.1 (C), 139.3 (C), 129.6 (Ar CH), 128.9 (Ar CH), 128.5 (Ar CH), 72.1 (CH$_2$), 59.3 (CH$_3$), 52.3 (CH), 44.4 (CH$_2$), 43.0 (CH$_2$), 38.8 (CH$_2$), 32.1 (CH$_2$); MS (FAB+) found m/z 308.21039 (M+H), C$_{15}$H$_{25}$N$_5$O$_2$ M+H calc. 308.20864.

Example 31

(S)—N$^G$-((Tetrahydrofuran-2-yl)methyl)-arginine tert-Butyl (2S)-2-Boc-amino-5-(N,N'-bis-Boc-N$^G$-((tetrahydrofuran-2-yl)methyl)guanidino)pentanoate (0.30 g, 0.5 mmol, 1 eq.), was dissolved in dioxane (3 mL). 4M HCl/dioxane (5 mL, 20 mmol, 40 eq) was added and the solution stirred for 48 hours. All excess reagents and solvents were removed in vacuo. The compound was purified by freeze-drying to yield a sticky, hygroscopic solid (74.2 mg, 67.3%). $^1$H NMR (d$_3$-MeOD): δ 1.64 (m, 2H); 1.79 (m, 2H); 1.93 (m, 2H); 1.98 (m, 2H); 3.44 (m, 2H); 3.58 (m, 1H); 3.88 (m, 2H); 3.93 (m, 1H); 4.00 (m, 2H). $^{13}$C NMR (d$_3$-MeOD): δ 25.8 (CH$_2$); 26.7 (CH$_2$); 28.8 (CH$_2$); 29.4 (CH$_2$); 41.9 (CH$_2$); 48.2 (CH$_2$); 54.1 (CH); 69.4 (CH). N.B. Values for C=N and C=O are too weak to be determined.

Example 32

(2S)-2-Amino-4-N$^G$-((tetrahydrofuran-2-yl)methyl)guanidinobutanoic acid

Synthesised using an adaptation of the procedure of Example 31. Yield 56.3%. $^1$H NMR (d$_3$-MeOD): δ 1.63 (m, 2H); 1.91 (m, 2H); 2.21 (m, 2H); 3.51 (t, J=6 Hz, 2H); 3.60 (t, J=6.3 Hz, 1H); 3.75 (m, 2H); 3.88 (m, 1H); 4.80 (t, J=7.5 Hz, 2H). $^{13}$C NMR (d$_3$-MeOD): δ 26.7 (CH$_2$); 29.9 (CH$_2$); 31.0 (CH$_2$); 39.0 (CH$_2$); 46.8 (CH$_2$); 51.4 (CH); 69.4 (CH$_2$); 70.7 (CH); 158.3 (C); 171.2 (C).

Example 33

2-Methoxybenzyl (S)-2-amino-4-[(N'-(2-methoxyethyl))guanidino]butanoate (2S)-2-Amino-4-N$^G$-(2-methoxyethyl)-guanidinobutanoic acid (100 mg, 0.34 mmol, 1 eq.) was dissolved in excess 2-methoxybenzyl alcohol (2 mL). The solution was cooled to 0° C. and thionyl chloride (0.2 mL, 2.75 mmol, 8 eq.) was added slowly. Once calm, the solution was heated to 70° C. for 48 hours. The product was purified by trituration (EtOAc) and freeze-dried to yield a sticky, hygroscopic solid (56.1 mg, 48%). $^1$H NMR (d$_3$-MeOD): δ 2.20 (m, 2H); 3.30 (m, 2H); 3.41 (m, 3H); 3.54 (m, 5H); 3.81 (m, 2H); 4.05 (t, J=6.3 Hz, 2H); 4.58 (m, 1H); 6.67 (m, 2H); 7.32 (m, 1H); 7.36 (m, 1H). $^{13}$C NMR (d$_3$-MeOD): δ 31.0 (CH$_2$); 39.1 (CH$_2$); 43.0 (CH$_2$); 51.8 (CH); 55.7 (CH$_3$); 59.2 (CH$_3$); 60.4 (CH$_2$); 72.1 (CH$_2$); 111.2; 112.3; 121.4; 129.0; 129.6; 132.1 (Aromatic Peaks); 158.2 (C); 171.4 (C). LCMS: 339.4 (M+H).

Example 34

4-Methoxybenzyl (S)-2-amino-4-[(N'-(2-methoxyethyl))guanidino]butanoate

Synthesised using an adaptation of the procedure of Example 33. Yield 80%. $^1$H NMR (d$_3$-MeOD): δ 2.22 (m, 2H); 3.30 (m, 2H); 3.41 (m, 2H); 3.52 (m, 5H); 3.77 (m, 5H); 4.43 (m, 1H); 6.96 (m, 2H); 7.25 (m, 2H). $^{13}$C NMR (d$_3$-MeOD): δ 31.0 (CH$_2$); 39.0 (CH$_2$); 43.0 (CH$_2$); 43.8 (CH$_2$); 51.4 (CH); 55.7 (CH$_3$); 59.3 (CH$_3$); 72.2 (CH$_2$); 114.8; 115.3; 115.6; 129.9; 130.6; 133.0 (Aromatic Peaks); 158.3 (C); 171.2 (C). LCMS: 339.3 (M+H).

Example 35

2-Fluorobenzyl (S)-2-amino-4-[(N'-(2-methoxyethyl))guanidino]butanoate

Synthesised using an adaptation of the procedure of Example 33. Yield 42.7%. $^1$H NMR (d$_3$-MeOD): δ 2.20 (m, 2H); 3.30 (m, 2H); 3.39 (m, 5H); 3.52 (m, 2H); 4.06 (t, J=7.4 Hz, 1H); 4.20 (t, J=7.0 Hz, 1H); 4.66 (s, 1H); 7.19 (m, 2H); 7.47 (m, 2H). $^{13}$C NMR (d$_3$-MeOD): δ 31.0 (CH$_2$); 39.0 (CH$_2$); 43.0 (CH$_2$); 51.5 (CH); 58.7; 59.2 (CH$_3$); 63.2 (CH$_2$); 72.1 (CH$_2$); 116.7; 117.1; 125.7; 130.5; 131.0; 133.2 (Aromatic Peaks); 158.3 (C); 171.9 (C). LCMS: 327.3 (M+H).

Example 36

3-Trifluoromethyl-4-fluorobenzyl (S)-2-amino-4-[(N'-(2-methoxyethyl))guanidino]butanoate Synthesised using an adaptation of the procedure of Example 33. Yield 28.3%. $^1$H NMR (d$_3$-MeOD): δ 2.05 (m, 2H); 3.31 (m, 2H); 3.40 (m, 5H); 3.53 (m, 2H); 3.61 (m, 2H); 3.63 (m, 1H); 7.32 (m, 1H); 7.67 (m, 2H). $^{13}$C NMR (d$_3$-MeOD): δ 22.8; 32.2 (CH$_2$); 39.8 (CH$_2$); 42.3 (CH$_2$); 53.1 (CH); 59.2 (CH$_3$); 72.1 (CH$_2$); 158.1 (C). N.B. The integration values for the NMR revealed the presence of 50% starting material, indicating the reaction had not gone to completion. LCMS: 395.4 (M+H).

Example 37

3-Phenoxybenzyl (S)-2-amino-4-[(N'-(2-methoxyethyl))guanidino]butanoate

Synthesised using an adaptation of the procedure of Example 33. Yield 52.8%. $^1$H NMR (d$_3$-MeOD): δ 2.20 (m, 2H); 3.30 (m, 1H); 3.35 (m, 1H); 3.42 (m, 2H); 3.52 (m, 5H); 4.03 (t, J=7 Hz, 1H); 4.21 (t, J=7 Hz, 1H); 4.57 (s, 1H); 6.99 (m, 3H); 7.13 (m, 3H); 7.37 (m, 3H). $^{13}$C NMR (d$_3$-MeOD): δ 31.1 (CH$_2$); 39.1 (CH$_2$); 43.0 (CH$_2$); 51.6 (CH); 59.2 (CH$_3$); 69.0 (CH$_2$); 72.1 (CH$_2$); 118.1; 118.5; 119.8; 120.1; 122.7; 124.5; 124.8; 130.8; 131.0; 131.3; 138.3; 145.1 (Aromatic Peaks); 158.7 (C); 169.8 (C). LCMS: 401.3 (M+H).

Example 38

3-Methylbenzyl (S)-2-amino-4-[(N'-(2-methoxyethyl))guanidino]butanoate

Synthesised using an adaptation of the procedure of Example 33. Yield 64.1%. $^1$H NMR (d$_3$-MeOD): δ 2.22 (m, 2H); 2.32 (d, J=6.4 Hz, 3H); 3.30 (b, 2H); 3.35 (s, 2H); 3.38 (b, 2H); 3.45 (b, 2H); 3.51 (b, 3H); 4.55 (s, 1H); 7.13 (m, 4H). $^{13}$C NMR (d$_3$-MeOD): δ 21.5 (CH$_3$); 31.0 (CH$_2$); 38.9 (CH$_2$); 43.0 (CH$_2$); 51.6 (CH); 59.2 (CH$_3$); 69.6 (CH$_2$); 72.1 (CH$_2$); 125.1; 126.9; 128.9; 130.5; 136.2; 139.0 (Aromatic Peaks); 142.6 (C); 170.0 (C). LCMS: 323.3 (M+H).

Example 39

3-Trifluoromethylbenzyl (S)-2-amino-4-[(N'-(2-methoxyethyl))guanidino]butanoate

Synthesised using an adaptation of the procedure of Example 33. Yield 11.0%. $^1$H NMR (d$_3$-MeOD): δ 2.20 (m, 2H); 3.38 (m, 7H); 3.53 (t, J=4.7, 2H); 3.60 (t, J=7.1 Hz, 2H); 4.67 (s, 1H); 7.70 (m, 4H). The NMR integrations indicate the presence of 50% starting material and hence, it can be concluded that the reaction did not go to completion. LCMS: 377.4 (M+H).

Example 40

3-Fluorobenzyl (S)-2-amino-4-[(N'-(2-methoxyethyl))guanidino]butanoate

Synthesised using an adaptation of the procedure of Example 33. Yield 60.7%. $^1$H NMR (d$_3$-MeOD): δ 2.20 (m, 2H); 3.30 (m, 2H); 3.42 (m, 2H); 3.54 (m, 5H); 4.06 (t, J=6.5 Hz, 1H); 4.24 (t, J=6.9 Hz, 1H); 6.96 (m, 1H); 7.12 (m, 1H); 7.31 (m, 2H). $^{13}$C NMR (d$_3$-MeOD): δ 30.9 (CH$_2$); 38.9 (CH$_2$); 43.0 (CH$_2$); 51.6 (CH); 59.2 (CH); 64.4 (CH$_2$); 72.1 (CH$_2$); 114.5; 116.5; 123.4; 125.5; 131.0; 138.2 (Aromatic peaks); 169.8 (C); 171.3 (C). LCMS: 327.3 (M+H).

Example 41

2-Methoxyethyl (S)-2-amino-4-[(N'-(2-methoxyethyl))guanidino]butanoate

Synthesised using an adaptation of the procedure of Example 33. Yield 66.7%. $^1$H NMR (d$_3$-MeOD): δ 2.20 (m, 2H); 3.38 (s, 6H); 3.41 (t, J=5.1 Hz, 2H); 3.47 (t, J=5.1 Hz, 2H); 3.52 (t, J=5.1 Hz, 2H); 3.67 (t, J=5.1 Hz, 2H); 4.18 (t, J=7.5 Hz, 1H); 4.41 (m, 2H). $^{13}$C NMR (d$_3$-MeOD): δ 31.0 (CH$_2$); 43.0 (CH$_2$); 51.5 (CH); 59.1 (CH$_3$); 59.2 (CH$_3$); 64.3 (CH$_2$); 66.4 (CH$_2$); 71.0 (CH$_2$); 72.1 (CH$_2$); 158.1 (C); 169.9 (C). LCMS: 277.4 (M+H).

Results
Biological Screening
DDAH Activity Assay

Rat kidney was homogenized in PBS containing PMSF 1 mM, leupeptin 5 μg/ml, pepstatin 5 μg/ml, chymostatin 5 μg/ml, and the lysate was centrifuged (4000 rpm. 20 min then supernatant further centrifuged for 40000 rpm, 30 min, 4° C.). The supernatants were analyzed for DDAH activity; [$^{14}$C]L-NMMA (1 μmol/L) was added to the cell lysates (final volume 100 μl) and incubated for 1 h at 37° C. Dowex resin (0.5 ml) at neutral pH was immediately added to samples to terminate the reaction and bind unmetabolized L-NMMA. [$^{14}$C] Citrulline formation was determined by scintillation counting (Hewlett Packard). The results are shown in Tables 1 and 1A.

Cell Assays

RAW cells were grown to 70% confluence in T$_{150}$ flasks then stimulated with LPS (5 μg/ml), TNFα (10 ng/ml) and IFNγ (100 U/ml) for 24 h, cells were scraped in cold 100 mM Tris (pH 7.6), 1 mM DTT, PMSF 1 mM, leupeptin 5 μg/ml, pepstatin 5 μg/ml, chymostatin 5 μg/ml and CaCl$_2$ 200 μM. Cells were lysed by three cycles of freeze/thaw and cleared by microcentrifugation. Protein concentration in the supernatants was determined by Biorad protein assay prior to use in the NOS assay.

Cell Viability Assay

RAW cells were treated with DDAH inhibitor compound (0.5 mM) in complete media for 24 h; cells were subsequently assessed for viability by MTT assay. Cell culture media was removed from cells and replaced with 200 μl complete media containing 3-[4,5-Dimethylthiazol-2-yl]-2,5-diphenyltetrazolium bromide (MTT 0.2 mg/ml) for 30 min at 37° C. MTT containing media was removed and 100 ul DMSO was added to solubilize cells; after shaking, plates were read at OD$_{550}$ nm.

There was no significant difference between untreated cells and those exposed to DDAH inhibitors. The results of the assay are shown in Table 2.

iNOS Activity Griess Assay

RAW cells were stimulated for 24 h with LPS/IFN and TNF, in the presence of the DDAH inhibitor compounds (0.5 mM). Levels of NOx secreted into the media by the cells were determined by Griess assay: Griess reagent [1:1 sulfanilamide (10%) in ortho-phosphoric acid (50%) and N-(1-napthyl)ethylenediamine dihydrochloride (1%)] was added as 100 μl volume to 100 μl cell culture media and the plate was read at 550 nm and analysed in relation to sodium nitrite and nitrate standards.

There was no significant difference between untreated cells and those exposed to DDAH inhibitors (n=10). The results of the assay are shown in Table 3.

eNOS Assay

Compounds to be tested were added to NOS assay buffer (HEPES 50 mM pH 7.2, FAD 5 μM, FMN 5 μM, BH$_4$ 10 μM, NADPH 1 mM, DTT 0.5 mM, CaCl$_2$ 1 mM, MgCl$_2$ 1 mM, calmodulin 50 nM, [$^{14}$C] arginine 100 μM) in a final volume of 100 μl and the reaction was initiated by addition of eNOS (eNOS 3.3. U/reaction, Alexis Biochemicals). Reactions were incubated for 1 h at 37° C. and the reaction was terminated by the addition of Dowex pH 5.5 (0.85 ml) to each tube. Tubes were vortexed and microfuged <12000 g, 5 min. 100 μl of the Dowex supernatant was added to 5 ml scintillation cocktail and was counted in a scintillation counter (Hewlett Packard). The compounds were tested at 1 mM and 0.1 mM concentrations. Activity is expressed as % of control where control contained no inhibitor, n=4. The DDAH inhibitors of the present invention tested had no significant effect on eNOS activity. The results are shown in Table 4.

In Vivo Studies

Male Wistar rats (250-300 g; Charles River, Margate, Kent, UK) were anaesthetised using Isoflurane. The jugular vein was cannulated. Animals were injected intravenously with a bolus dose of inhibitor (60 mg/kg) or saline. Anaesthesia was maintained for 4 hours at the end of which blood was obtained via cardiac puncture for the determination of serum dimethylarginine levels. [All animals received care in compliance with The British Home Office Regulations and Principles of Laboratory Animal Care. (Project licenses PPL/5344, PPL/4824, PPL 70/5580)]

The results of the study are shown in Table 5.

As can be seen from Table 5, ADMA levels were higher in the treated animals, which is consistent with the inhibition of DDAH. SDMA is not a substrate for DDAH and the levels of SDMA would be expected to be the same of the treated and the control animals, and this was the case. Since there is a great deal of variability of the "normal" ADMA and SDMA level, it is useful to measure the ratio of ADMA and SDMA in each animal to provide a reliable indicator of the relative changes of these to substances.

Inhibition of DDAH Reduces Peritoneal Inflammation

The effects of a DDAH inhibitor on zymosan-induced peritonitis were tested in two different strains of mice. C57/Blk6 or TO mice, male 8-10 weeks were placed in a heat box for 10 mins at 38° C., and treated with 60 mg/kg of SR291 [NA-(2-methoxyethyl)-L-arginine methyl ester] i.v. 30 mins later they were given 1 mg of zymosan i.p. A second dose of SR291 (60 mg/kg) was administered 2 h later and after 4 h mice were anesthetised with isofluorane and blood withdrawn by cardiac puncture. Mice were sacrificed and had 2 mls of ice cold PBS injected into their peritoneal cavity, the cavity was then gently massaged and cut open, the peritoneal washout was harvested and put on ice. Blood was spun down at 400 g, 10 mins at 4° C. The cells were spun at 4000 rpm for 5 mins at 4° C. Plasma was removed from the blood and frozen at −80° C. The exudates from the washout were removed and frozen at −80° C., the cell pellet was resuspended in 1 ml ice cold PBS and were counted on a haemocytometer. The cells were spun as before, the supernatant discarded and the cells frozen at −80° C. Polymorphonuclear (PMN) cell infiltrate into the peritoneal cavity was used to measure inflammation. In three separate experiments each involving 8-12 mice (half treated with saline half with active drug) SR291 significantly reduced PMN infiltrate. The results of the study are shown in Tables 5 to 10. Table 6 shows the results obtained for zymosan peritonitis (C57's male 8-10 weeks) 60 mg/kg SR 291 iv −30 min taken off at 4 hrs. Table 7 shows the cumulative results of the dataset that appears in Table 6. Table 8 shows a combination of two datasets for the C57 mice. Table 9 shows the results obtained for zymosan peritonitis (TO mice male 8-10 weeks) 60 mg/kg SR291 iv −30 min, +2 hrs. Taken off at 4 hrs. Table 10 shows the cumulative results of the dataset that appears in Table 9. Table 11 shows the results of a second study obtained for zymosan peritonitis (TO mice male 8-10 weeks) 60 mg/kg SR 291 iv −30 min, +2 hrs. Taken off at 4 hrs. Table 12 shows the cumulative results of the dataset that appears in Table 11. Table 13 shows the cumulative results of the two datasets that appear in Tables 9 and 11.

DDAH Inhibition Restores Vascular Reactivity and Maintains BP in Endotoxaemia

Effects of two compounds SR 291 [$N^G$-(2-methoxyethyl)-L-arginine methyl ester] and SR 257 [$N^G$-(2-methoxyethyl)-L-arginine]) have been tested in a series of models of endotoxin-induced vascular dysfunction. Treatment of rat aortic vascular rings in static culture with endotoxin (10 µg/ml) led to an increase in generation of nitric oxide (as measured by nitrite and nitrate). This increase in NO was prevented by treatment with 500 µM SR257 or SR291. The results of this study are shown in FIG. 1.

Figure 2A:
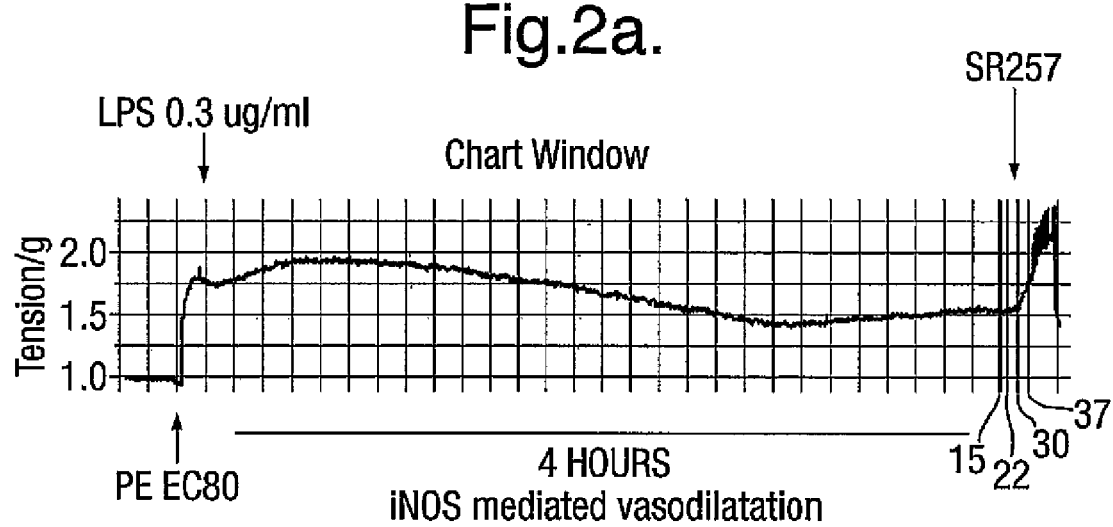
FIGS. 2a and 2b are traces illustrating the tension in isolated aortic ring demonstrating contraction in response to phenylephrine EC80 and subsequent iNOS mediated dilatation in response to LPS treatment over 4 hour timecourse (FIG. 2a) and response of vessel to D-SR257, L-SR257 and L-arginine (FIG. 2b—expanded trace from 2a)
Figure 2B:
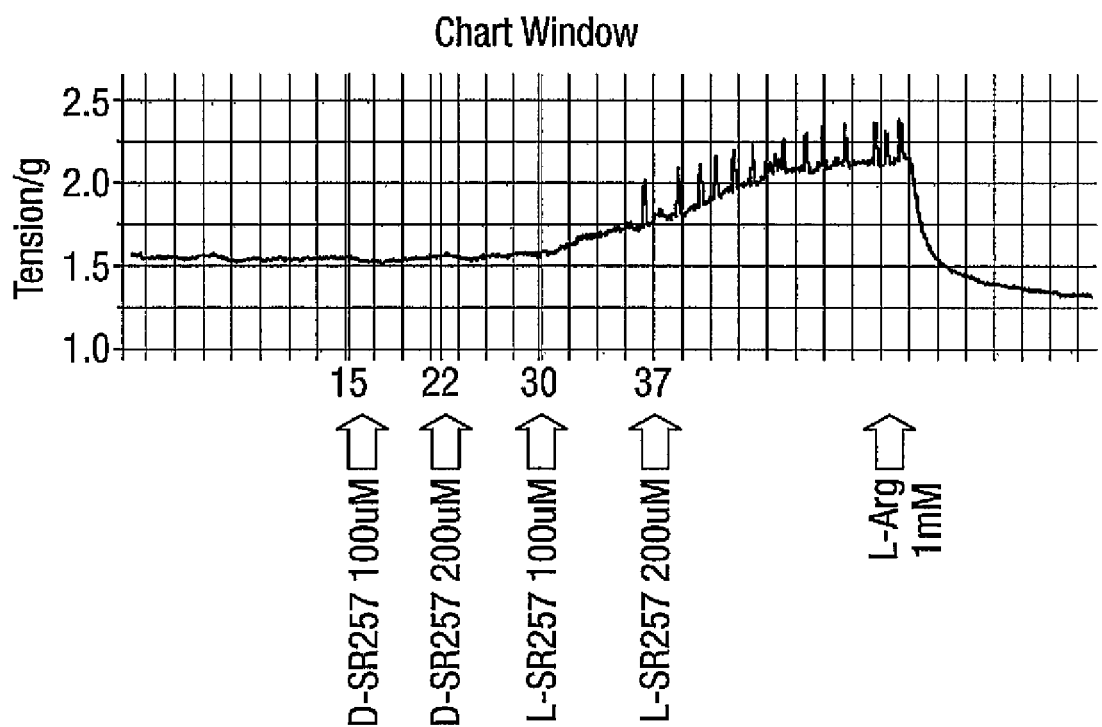

Incubation of rat aortic rings with endotoxin (0.3 µg/ml) led to the development of hyporeactivity to vasoconstrictors. This effect was reversed dose dependently by inhibition of DDAH using 100 µM and 200 µM SR291 or SR257 whilst the inactive D-isomers of each compound showed no effect. This is shown in FIGS. 2a and 2b.

Figure 3:
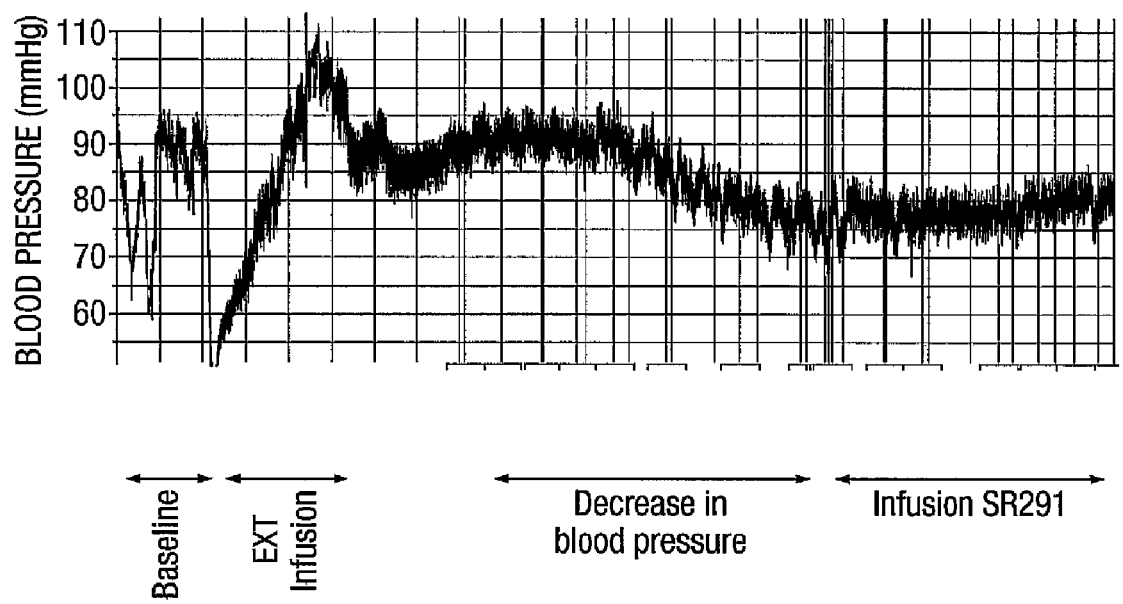
FIG. 3 is a trace illustrating blood pressure in anaesthetized rat demonstrating initial effect of 40 mg/kg endotoxin (ETX) administration on blood pressure followed by a recovery and gradual fall in blood pressure over time. Effects of intervention after 2-3 hours (when blood pressure had fallen to 80% of baseline pre LPS blood pressure) with 30 mg/kg/hr infusion of SR291.

Injection of endotoxin (40 mg/kg) into rats caused a progressive fall in systemic BP. The decline was halted by infusion of 30 mg/kg/hr SR291. This is shown in FIG. 3.

These data show that inhibition of DDAH may be used to prevent vascular collapse in sepsis.

TABLE 1

| Compound Name | Inhibition at 1 mM, % | $IC_{50}$, µM |
|---|---|---|
| (S)-2-Amino-4-(N'-isopropylguanidino)butanoic acid | 38 | |
| (S)-2-Amino-4-(N'-propylguanidino)butanoic acid | 41 | |
| (S)-2-Amino-4-(N'-2,2-dimethylpropyl)guanidino)butanoic acid | 19 | |
| (S)-2-Amino-4-(N'-octylguanidino)butanoic acid | 27 | |
| (S)-2-Amino-4-(N'-cyclohexylguanidino)butanoic acid | 51 | 1470 |
| (S)-2-Amino-4-(N'-(2-methoxyethyl)guanidino)butanoic acid | 90 | 189 |
| (S)-2-Amino-4-(N'-(2-phenoxyethyl)guanidino)butanoic acid | 38 | |
| (S)-2-Amino-4-(N'-(2-isopropoxyethyl)guanidino)butanoic acid | 97 | 301 |
| (S)-2-Amino-4-(N'-(2-methylthioethyl)guanidino)butanoic acid | 19 | |
| (S)-2-Amino-4-(N'-phenylguanidino)butanoic acid | 65 | 1000 |
| (S)-2-Amino-4-(N'-benzylguanidino)butanoic acid | 22 | |
| (S)-2-Amino-4-(N'-(2-thiophenemethyl)guanidino)butanoic acid | 34 | |
| (S)-2-Amino-4-(N'-allylguanidino)butanoic acid | 70 | 998 |
| (S)-2-Amino-4-(N'-(2'-dimethylaminoethyl)guanidino)butanoic acid | 25 | |
| (S)-2-Amino-4-(N'-cyclopropylguanidino)butanoic acid | 65 | 1020 |
| (S)-2-Amino-4-[(piperidine-1-carboximidoyl)-amino]butanoic acid | 74 | 264 |
| (S)-2-Amino-4-[(morpholine-4-carboximidoyl)-amino]butanoic acid | 60 | 686 |
| (S)-2-Amino-4-[(pyrrolidine-1-carboximidoyl)-amino]butanoic acid | 79 | 500 |
| $N^G$-(2-methoxyethyl)-L-arginine | 100 | 22 |
| $N^G$-(2-methoxyethyl)-L-arginine methyl ester | 83 | 20 |
| (S)-2-Amino-4-(N'-(2-methoxyethyl)guanidino)butanoic acid methyl ester | 75 | 96 |
| (S)-2-Amino-4-(N'-(2-methoxyethyl)guanidino)butanoic acid ethyl ester | 44 | 159 |
| (S)-2-Amino-4-(N'-(2-methoxyethyl)guanidino)butanoic acid propyl ester | 64 | 111 |
| (S)-2-Amino-4-(N'-(2-methoxyethyl)guanidino)butanoic acid butyl ester | 40 | 113 |
| (S)-2-Amino-4-(N'-(2-methoxyethyl)guanidino)butanoic acid benzyl ester | 96 | 27 |

TABLE 1A

| Compound Name | Inhibition at 100 µM (%) |
|---|---|
| (S)-$N^G$-((Tetrahydrofuran-2-yl)methyl)-arginine | 30 |
| (2S)-2-Amino-4-$N^G$-((tetrahydrofuran-2-yl)methyl)guanidinobutanoic acid | 10 |
| 2-Methoxybenzyl (S)-2-amino-4-[(N'-(2-methoxyethyl))guanidino] butanoate | 47.4 |
| 4-Methoxybenzyl (S)-2-amino-4-[(N'-(2-methoxyethyl))guanidino] butanoate | 22.1 |
| 2-Fluorobenzyl (S)-2-amino-4-[(N'-(2-methoxyethyl))guanidino]butanoate | 39.8 |
| 3-Trifluoromethyl-4-fluorobenzyl (S)-2-amino-4-[(N'-(2-methoxyethyl))guanidino] butanoate | 50.6 |
| 3-Phenoxybenzyl (S)-2-amino-4-[(N'-(2-methoxyethyl))guanidino] butanoate | 42.7 |
| 3-Methylbenzyl (S)-2-amino-4-[(N'-(2-methoxyethyl))guanidino] butanoate | 48.7 |

TABLE 1A-continued

| Compound Name | Inhibition at 100 μM (%) |
|---|---|
| 3-Trifluoromethylbenzyl (S)-2-amino-4-[(N'-(2-methoxyethyl))guanidino] butanoate | 45.3 |
| 3-Fluorobenzyl (S)-2-amino-4-[(N'-(2-methoxyethyl))guanidino] butanoate | 33.2 |
| 2-Methoxyethyl (S)-2-amino-4-[(N'-(2-methoxyethyl))guanidino] butanoate | 59 |

TABLE 2

| | OD units drug ± sd | Number of experiments |
|---|---|---|
| Control | 2.54 ± 0.26 | 3 |
| (S)-2-Amino-4-(N'-(2 methoxyethyl)guanidino)butanoic acid methyl ester | 2.33 ± 0.19 | 3 |
| (S)-2-Amino-4-(N'-(2-methoxyethyl)guanidino)butanoic acid propyl ester | 2.40 ± 0.21 | 3 |
| (S)-2-Amino-4-(N'-(2-methoxyethyl)guanidino)butanoic acid benzyl ester | 2.40 ± 0.17 | 3 |
| $N^G$-(2-methoxyethyl)-L-arginine | 2.15 ± 0.13 | 3 |
| $N^G$-(2-methoxyethyl)-L-arginine methyl ester | 2.41 ± 0.10 | 3 |
| L-N-5-(1-iminoethyl)ornithine [NIO] | 1.89 ± 0.41 | 3 |
| ADMA | 2.22 ± 0.10 | 3 |
| L-NMMA | 2.22 ± 0.08 | 3 |

TABLE 3

| | OD units drug ± sd | Number of experiments |
|---|---|---|
| Control | 0.367 ± 0.021 | 5 |
| (S)-2-Amino-4-(N'-(2 methoxyethyl)guanidino)butanoic acid methyl ester | 0.329 ± 0.013 | 5 |
| (S)-2-Amino-4-(N'-(2-methoxyethyl)guanidino)butanoic acid propyl ester | 0.351 ± 0.013 | 5 |
| (S)-2-Amino-4-(N'-(2-methoxyethyl)guanidino)butanoic acid benzyl ester | 0.327 ± 0.026 | 5 |
| $N^G$-(2-methoxyethyl)-L-arginine | 0.326 ± 0.014 | 5 |
| $N^G$-(2-methoxyethyl)-L-arginine methyl ester | 0.325 ± 0.009 | 5 |
| NIO | 0.103 ± 0.002 | 5 |
| ADMA | 0.195 ± 0.014 | 5 |
| L-NMMA | 0.121 ± 0.003 | 5 |

TABLE 4

| | % of control ± sd [number of experiments] | |
|---|---|---|
| | 1 mM | 0.1 mM |
| Control | 100.0 ± 14.95 [6] | 100.0 ± 14.95 [6] |
| (S)-2-Amino-4-(N'-(2 methoxyethyl)-guanidino)butanoic acid methyl ester | 84.05 ± 8.09 [4] | 87.23 ± 18.05 [2] |
| (S)-2-Amino-4-(N'-(2-methoxyethyl)-guanidino)butanoic acid propyl ester | 93.97 ± 12.93 [4] | 113.5 ± 7.93 [2] |
| (S)-2-Amino-4-(N'-(2-methoxyethyl)-guanidino)butanoic acid benzyl ester | 82.88 ± 10.08 [4] | 101.2 ± 38.07 [2] |
| $N^G$-(2-methoxyethyl)-L-arginine | 84.81 ± 22.74 [4] | 96.84 ± 30.49 [2] |
| $N^G$-(2-methoxyethyl)-L-arginine methyl ester | 112.5 ± 27.47 [4] | 120.8 ± 17.80 [2] |
| NIO | 6.25 ± 7.52 [5] | 4.14 ± 8.74 [3] |
| L-NMMA | 16.17 ± 15.78 [4] | |

TABLE 5

| | ADMA:SDMA ± sd | Number of experiments |
|---|---|---|
| Control | 1.81 ± 0.23 | 9 |
| $N^G$-(2-methoxyethyl)-L-arginine | 3.50 ± 0.48 | 8 |
| $N^G$-(2-methoxyethyl)-L-arginine methyl ester | 2.73 ± 0.44 | 4 |

TABLE 6

| | cells million/ml | | | | |
|---|---|---|---|---|---|
| drug | 1 | 2 | 3 | 4 | 5 |
| Saline | 14 | 12 | 7 | 6.5 | 6 |
| SR291 | 3 | 4 | 4.5 | 6.5 | 9 |

TABLE 7

| | cells million/ml | |
|---|---|---|
| | mean | SEM |
| Saline | 9.1 | 1.631 |
| SR291 | 5.4 | 1.0654 |

TABLE 8

| | cells $10^6$/ml | |
|---|---|---|
| | mean | sem |
| saline | 6.7455 | 0.9746 |
| SR291 | 4.2 | 0.6097 |

TABLE 9

| | cells $10^6$/ml | | | | | |
|---|---|---|---|---|---|---|
| animal | 1 | 2 | 3 | 4 | 5 | 6 |
| Saline | 4.2 | 5 | 4.9 | 4.8 | 4.75 | 5.05 |
| SR291 | 3.05 | 3.35 | 3.2 | 1.4 | 3.9 | 4.3 |

TABLE 10

| | cells $10^6$/ml | |
|---|---|---|
| | mean | sem |
| Saline | 4.783333 | 0.12561 |
| SR291 | 3.2 | 0.407636 |

TABLE 11

| | cells $10^6$/ml | | | | | |
|---|---|---|---|---|---|---|
| | 1 | 2 | 3 | 4 | 5 | 6 |
| Saline | 6 | 6.15 | 6.5 | 6.3 | 5.9 | 5.9 |
| SR291 | 4.3 | 4.6 | 4.85 | 5.2 | 4.3 | 3.9 |

TABLE 12

| | cells $10^6$/ml | |
|---|---|---|
| | mean | sem |
| Saline | 6.125 | 0.098107 |
| SR291 | 4.525 | 0.187861 |

TABLE 13

| | cells $10^6$/ml | |
|---|---|---|
| | mean | sem |
| saline | 5.454167 | 0.216065 |
| SR291 | 3.8625 | 0.292723 |

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A compound of formula (I) or a pharmaceutically acceptable salt thereof, (I)

wherein:
R$^1$ is -L-Het-L', -L-Y-L', -L-Het-A or -L-Y-A; wherein:
L is $C_1$-$C_6$ alkyl, $C_2$-$C_6$ alkenyl or $C_2$-$C_6$ alkynyl;
L' is $C_1$-$C_6$ alkyl, $C_2$-$C_6$ alkenyl or $C_2$-$C_6$ alkynyl;
A is $C_6$-$C_{10}$ aryl, $C_3$-$C_8$ carbocyclyl, 5- to 10-membered heterocyclyl or 5- to 10-membered heteroaryl;
Het is —O—, —S— or —NR'—, wherein R' is hydrogen, $C_1$-$C_6$ alkyl, $C_2$-$C_6$ alkenyl, or $C_2$-$C_6$ alkynyl;
Y is —CO—, —SO—, —SO$_2$—, —CO—O—, —CO—NR'—, —O—CO— or —NR'-CO—, wherein R' is defined as above;
R$^2$ is hydrogen, $C_1$-$C_6$ alkyl, $C_2$-$C_6$ alkenyl or $C_2$-$C_6$ alkynyl; and
R$^3$ is hydrogen, $C_1$-$C_6$ alkyl, $C_2$-$C_6$ alkenyl or $C_2$-$C_6$ alkynyl;
R$^4$ is hydrogen, $C_1$-$C_6$ alkyl, $C_2$-$C_6$ alkenyl or $C_2$-$C_6$ alkynyl;
B is $C_1$-$C_6$ alkyl, $C_2$-$C_6$ alkenyl, —O-L-, —S-L- or -L-Het-L'-; wherein L, L' and Het are as defined above;
X is —O—, —S— or —NR'-; wherein R' is as defined above;
R$^5$ is hydrogen, $C_1$-$C_6$ alkyl, $C_2$-$C_6$ alkenyl, $C_2$-$C_6$ alkynyl, aryl, $C_3$-$C_8$ carbocyclyl, 5- to 10-membered heterocyclyl, 5- to 10-membered heteroaryl, -L-A, -L-Het-L', -L-Y-L', -L-Het-A, -L-Y-A, -L-A-Het-A, -L-A-L'-A or -L-A-Het-L'-A; wherein L, L', Het and Y are as defined above and wherein each A is the same or different and is as defined above;
R$^6$ is hydrogen, $C_1$-$C_6$ alkyl, $C_2$-$C_6$ alkenyl or $C_2$-$C_6$ alkynyl;
R$^7$ is hydrogen, $C_1$-$C_6$ alkyl, $C_2$-$C_6$ alkenyl or $C_2$-$C_6$ alkynyl; and
R$^8$ is hydrogen, $C_1$-$C_6$ alkyl, $C_2$-$C_6$ alkenyl or $C_2$-$C_6$ alkynyl;
wherein:
the alkyl, alkenyl and alkynyl groups and moieties in the substituents R$^1$ to R$^7$, X and B are unsubstituted or substituted by one, two or three substituents which are the same or different and are independently selected from the group consisting of halogen, hydroxy, amino and thio substituents; and
the aryl, carbocyclyl, heterocyclyl and heteroaryl groups and moieties in the substituents R$^1$ and R$^5$ are unsubstituted or substituted by one, two or three substituents independently-selected from the group consisting of halogen, hydroxy, amino, thio, $C_1$-$C_6$ alkyl, $C_1$-$C_6$ alkoxy, $C_1$-$C_6$ alkylthio, nitro, cyano, $C_1$-$C_6$ alkylamino, di-($C_1$-$C_6$ alkyl)amino, $C_1$-$C_6$ haloalkyl, $C_1$-$C_6$ haloalkoxy and $C_1$-$C_6$ haloalkylthio substituents.

2. A compound according to claim 1 wherein the compound of formula (I) is a compound of formula (II)

(II)

wherein:
R$^{11}$ is —($C_1$-$C_2$ alkyl)-O-phenyl, —($C_1$-$C_2$ alkyl)-O—($C_1$-$C_4$ alkyl), —($C_1$-$C_2$ alkyl)-S($C_1$-$C_2$ alkyl) or —($C_1$-$C_2$ alkyl)-NMe-($C_1$-$C_2$ alkyl);
R$^{21}$ is hydrogen, methyl or ethyl;
B$^1$ is a 1,2-ethyl or 1,3-propyl moiety; and
R$^{51}$ is hydrogen, $C_1$-$C_4$ alkyl, —($C_1$-$C_2$ alkyl)-phenyl, —($C_1$-$C_2$ alkyl)-O—($C_1$-$C_2$ alkyl) or —($C_1$-$C_2$ alkyl)-phenyl-O-phenyl;
wherein:
the alkyl groups and moieties in the substituents R$^{11}$, R$^{21}$, B and R$^{51}$ are unsubstituted or substituted by a single fluoro substituent; and the phenyl group in R$^{11}$ is unsubstituted and the phenyl groups in $R^{51}$ are unsubstituted or substituted by one or two substituents selected from fluorine, $C_1$-$C_2$ alkyl, $C_1$-$C_2$ alkoxy and $C_1$-$C_2$ haloalkyl substituents.

3. A compound according to claim 2 wherein $R^{11}$ is —($C_1$-$C_2$ alkyl)-O—($C_1$-$C_4$ alkyl).

4. A compound according to claim 2 wherein $R^{51}$ is $C_1$-$C_4$ alkyl or —($C_1$-$C_2$ alkyl)-phenyl.

5. A compound according to claim 1 wherein A is phenyl, $C_3$-$C_6$ carbocyclyl, 5- to 6-membered heterocyclyl or 5- to 6-membered heteroaryl.

6. A compound according to claim 1 wherein L and L' are the same or different and are $C_1$-$C_6$ alkyl.

7. A compound according to claim 1 wherein B is $C_2$-$C_6$ alkyl.

8. A compound according to claim 1 wherein $R^5$ is hydrogen, $C_1$-$C_6$ alkyl, $C_2$-$C_6$ alkenyl, phenyl, $C_3$-$C_6$ carbocyclyl, 5- to 6-membered heterocyclyl, 5- to 6-membered heteroaryl, -L-A, -L-Het-L', -L-Y-L', -L-Het-A, -L-Y-A or -L-A-Het-A.

9. A compound according to claim 1 which is $N^G$-(2-methoxyethyl)-L-arginine or $N^G$-(2-methoxyethyl)-L-arginine methyl ester, or a pharmaceutically acceptable salt thereof.

10. A pharmaceutical composition comprising a compound of formula (I), as defined in claim 1, or a pharmaceutically acceptable salt thereof, and a pharmaceutically acceptable carrier or diluent.

11. A method of treating a patient suffering from ischaemia-reperfusion injury of the brain or heart, asthma, pain, peritonitis or sepsis, which method comprises administering to said patient an effective amount of a compound of formula (I) or a pharmaceutically acceptable salt thereof,

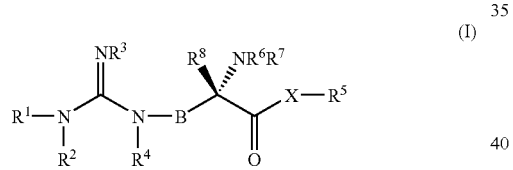

(I)

wherein:
$R^1$ is -L-Het-L', -L-Y-L', -L-Het-A or -L-Y-A; wherein:
L is $C_1$-$C_6$ alkyl, $C_2$-$C_6$ alkenyl or $C_2$-$C_6$ alkynyl;
L' is $C_1$-$C_6$ alkyl, $C_2$-$C_6$ alkenyl or $C_2$-$C_6$ alkynyl;
A is $C_6$-$C_{10}$ aryl, $C_3$-$C_8$ carbocyclyl, 5- to 10-membered heterocyclyl or 5- to 10-membered heteroaryl;
Het is —O—, —S— or —NR'—, wherein R' is hydrogen, $C_1$-$C_6$ alkyl, $C_2$-$C_6$ alkenyl, or $C_2$-$C_6$ alkynyl;
Y is —CO—, —SO—, —SO$_2$—, —CO—O—, —CO—NR'—, —O—CO— or —NR'—CO—, wherein R' is defined as above;
$R^2$ is hydrogen, $C_1$-$C_6$ alkyl, $C_2$-$C_6$ alkenyl or $C_2$-$C_6$ alkynyl; and
$R^3$ is hydrogen, $C_1$-$C_6$ alkyl, $C_2$-$C_6$ alkenyl or $C_2$-$C_6$ alkynyl;
$R^4$ is hydrogen, $C_1$-$C_6$ alkyl, $C_2$-$C_6$ alkenyl or $C_2$-$C_6$ alkynyl;
B is $C_1$-$C_6$ alkyl, $C_2$-$C_6$ alkenyl, —O-L-, —S-L- or -L-Het-L'-; wherein L, L' and Het are as defined above;
X is —O—, —S— or —NR'—; wherein R' is as defined above;

$R^5$ is hydrogen, $C_1$-$C_6$ alkyl, $C_2$-$C_6$ alkenyl, $C_2$-$C_6$ alkynyl, aryl, $C_3$-$C_8$ carbocyclyl, 5- to 10-membered heterocyclyl, 5- to 10-membered heteroaryl, -L-A, -L-Het-L', -L-Y-L', -L-Het-A, -L-Y-A, -L-A-Het-A, -L-A-L'-A or -L-A-Het-L'-A; wherein L, L', Het and Y are as defined above and wherein each A is the same or different and is as defined above;
$R^6$ is hydrogen, $C_1$-$C_6$ alkyl, $C_2$-$C_6$ alkenyl or $C_2$-$C_6$ alkynyl;
$R^7$ is hydrogen, $C_1$-$C_6$ alkyl, $C_2$-$C_6$ alkenyl or $C_2$-$C_6$ alkynyl; and
$R^8$ is hydrogen, $C_1$-$C_6$ alkyl, $C_2$-$C_6$ alkenyl or $C_2$-$C_6$ alkynyl;
wherein:
the alkyl, alkenyl and alkynyl groups and moieties in the substituents $R^1$ to $R^7$, X and B are unsubstituted or substituted by one, two or three substituents which are the same or different and are independently selected from the group consisting of halogen, hydroxy, amino and thio substituents; and
the aryl, carbocyclyl, heterocyclyl and heteroaryl groups and moieties in the substituents $R^1$ and $R^5$ are unsubstituted or substituted by one, two or three substituents independently-selected from the group consisting of halogen, hydroxy, amino, thio, $C_1$-$C_6$ alkyl, $C_1$-$C_6$ alkoxy, $C_1$-$C_6$ alkylthio, nitro, cyano, $C_1$-$C_6$ alkylamino, di-($C_1$-$C_6$ alkyl)amino, $C_1$-$C_6$ haloalkyl, $C_1$-$C_6$ haloalkoxy and $C_1$-$C_6$ haloalkylthio substituents.

12. The method according to claim 11 wherein the disease is peritonitis or sepsis.

13. The method according to claim 11 wherein the compound of formula (I) is a compound of formula (II),

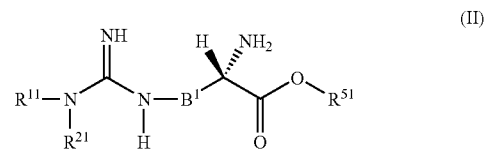

(II)

wherein:
$R^{11}$ is —($C_1$-$C_2$ alkyl)-O-phenyl, —($C_1$-$C_2$ alkyl)-O—($C_1$-$C_4$ alkyl), —($C_1$-$C_2$ alkyl)-S($C_1$-$C_2$ alkyl) or —($C_1$-$C_2$ alkyl)-NMe-($C_1$-$C_2$ alkyl);
$R^{21}$ is hydrogen, methyl or ethyl;
$B^1$ is a 1,2-ethyl or 1,3-propyl moiety; and
$R^{51}$ is hydrogen, $C_1$-$C_4$ alkyl, —($C_1$-$C_2$ alkyl)-phenyl, —($C_1$-$C_2$ alkyl)-O—($C_1$-$C_2$ alkyl) or —($C_1$-$C_2$ alkyl)-phenyl-O-phenyl;
wherein:
the alkyl groups and moieties in the substituents $R^{11}$, $R^{21}$, B and $R^{51}$ are unsubstituted or substituted by a single fluoro substituent; and the phenyl group in $R^{11}$ is unsubstituted and the phenyl groups in $R^{51}$ are unsubstituted or substituted by one or two substituents selected from fluorine, $C_1$-$C_2$ alkyl, $C_1$-$C_2$ alkoxy and $C_1$-$C_2$ haloalkyl substituents.

14. The method of claim 11 wherein the compound is $N^G$-(2-methoxyethyl)-L-arginine, $N^G$-(2-methoxyethyl)-L-arginine methyl ester, or a pharmaceutically acceptable salt thereof.

* * * * *